United States Patent
Koga et al.

(10) Patent No.: US 10,523,905 B2
(45) Date of Patent: Dec. 31, 2019

(54) SUBSTRATE IMAGING APPARATUS

(71) Applicant: Tokyo Electron Limited, Tokyo (JP)

(72) Inventors: Norihisa Koga, Koshi (JP); Tadashi Nishiyama, Koshi (JP); Yasuaki Noda, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 369 days.

(21) Appl. No.: 15/437,869

(22) Filed: Feb. 21, 2017

(65) Prior Publication Data
US 2017/0244936 A1 Aug. 24, 2017

(30) Foreign Application Priority Data
Feb. 22, 2016 (JP) .................. 2016-031361

(51) Int. Cl.
*H04N 7/18* (2006.01)
*G01N 21/88* (2006.01)
(Continued)

(52) U.S. Cl.
CPC ......... *H04N 7/183* (2013.01); *G01N 21/8806* (2013.01); *G06T 7/0004* (2013.01);
(Continued)

(58) Field of Classification Search
CPC ........ G01N 2021/8812; G01N 21/8806; G06T 2207/30148; G06T 7/0004; H04N 5/2256;
(Continued)

(56) References Cited

U.S. PATENT DOCUMENTS 7,489,385 B2 2/2009 Banine
7,656,519 B2 * 2/2010 Meeks ................ G01B 11/065
356/237.2
(Continued)

FOREIGN PATENT DOCUMENTS

JP H11-339042 A 12/1999
JP 2007-155448 A 6/2007
(Continued)

OTHER PUBLICATIONS

Japanese Office Action (with English translation), Japanese Application No. 2016-031361, dated Aug. 6, 2019 (6 pages).

*Primary Examiner* — Tri T Ton
(74) *Attorney, Agent, or Firm* — Burr & Brown, PLLC

(57) ABSTRACT

In one embodiment, a substrate imaging apparatus includes: a rotary holding unit that holds and rotates a substrate; a mirror member having a reflecting surface that opposes an end face of the substrate and a peripheral portion of a back surface of the substrate held by the rotary holding unit, the reflecting surface being inclined with respect to a rotation axis of the rotary holding unit; and a camera having an imaging device that receives both first light and second light through a lens, the first light coming from a peripheral portion of a front surface of the substrate held by the rotary holding unit, and the second light being a reflected light of second light which comes from the end face of the substrate held by the rotary holding unit and is reflected by the reflecting surface.

12 Claims, 22 Drawing Sheets

(51) Int. Cl.
*G06T 7/00* (2017.01)
*H04N 5/225* (2006.01)
(52) U.S. Cl.
CPC ... *H04N 5/2256* (2013.01); *G01N 2021/8812* (2013.01); *G06T 2207/30148* (2013.01)
(58) Field of Classification Search
CPC ... H04N 7/183; G03F 7/7015; G03F 7/70225; G03F 7/70616; G03F 7/70833; H01L 21/0274; H01L 22/12
USPC ............. 356/239.1–239.8, 237.1–237.6
See application file for complete search history.

(56) References Cited

U.S. PATENT DOCUMENTS

| | | |
|---|---|---|
| 7,959,988 B2 | 6/2011 | Yamamoto et al. |
| 2008/0124489 A1 | 5/2008 | Yamamoto et al. |

FOREIGN PATENT DOCUMENTS

| | | |
|---|---|---|
| JP | 2007-251143 A | 9/2007 |
| JP | 2008-135583 A | 6/2008 |
| TW | 200426539 A | 12/2004 |

* cited by examiner

SUBSTRATE IMAGING APPARATUS

CROSS-REFERENCE TO RELATED APPLICATIONS

This application is based upon and claims the benefit of priority from Japanese Patent Application No. 2016-031361, filed on Feb. 22, 2016, the entire contents of which are incorporated herein by reference.

BACKGROUND OF THE INVENTION

Field of the Invention

The present invention relates to a substrate imaging apparatus.

Background Art

At present, a photolithography technique is widely used to form a pattern (patterned projections/recesses) on a substrate in fine processing of substrates. For example, a process for forming a resist pattern on a semiconductor wafer includes forming a resist film on a surface of the wafer, exposing the resist film with a predetermined pattern, and allowing the exposed resist film to be reacted with a developer to develop the exposed resist film.

In recent years, a liquid immersion exposure technique has been proposed as a technique for obtaining a very fine resist pattern of about 40 nm to 45 nm in line width. When a resist film is subjected to a liquid immersion exposure, the resist film is exposed while an exposure liquid (e.g., deionized water or the like), which has a refractive index higher than that of air, is supplied to a space between a wafer and a projection lens for exposure.

In the course of processing the wafer surface, small particles (foreign matters) may adhere to the wafer surface (its central portion or peripheral portion) for various reasons. Most particles can be removed by cleaning the substrate surface with a cleaning liquid, but some particles may remain on the substrate surface. When a wafer having particles adhered thereto is loaded into an exposure device, the exposure device is contaminated. In this case, when a succeeding wafer is exposed, a particle shape as well as a desired pattern may be transferred. In addition, when the exposure device is contaminated with particles, it may take a long time to clean the exposure device, which seriously lowers productivity. Moreover, if a wafer has some defect in the vicinity of its periphery (for example, flaw, crack, scratch, etc.) the wafer cannot be properly processed. Thus, Patent Document 1 (JP2007-251143A), Patent Document 2 (JP2008-135583A) and Patent Document 3 (JP11-339042A) each disclose a wafer inspection method including a step of taking images of a peripheral portion of a wafer by means of a plurality of cameras, a step of processing the images, and a step of judging the condition of the peripheral portion of the wafer based on the processed images.

However, in order to inspect surfaces (e.g., upper surface and end face) near the periphery of a wafer, the checking method of Patent Documents 1 to 3 takes images the surfaces individually, with the use of the plurality of cameras. Thus, since a large space for installation of these cameras is needed, the wafer inspection apparatus may have a larger size as well as an increased cost of the apparatus.

It is conceivable that the plurality of surfaces near the peripheral portion of the wafer are inspected by moving one camera. However, since a space for installation of a mechanism for moving the camera is needed, the apparatus may have a larger size after all. In addition, since the moving speed of the camera is not so high, it takes a long time to inspect the wafer.

Further, if a plurality of cameras are used, a mechanism for assembling the cameras is needed in addition to these cameras, which complicates the structure. Also if one camera is moved, a mechanism for moving the camera is needed in addition to the camera, which complicates the structure. Thus, in the inspection method of Patent Documents 1 to 3, a malfunction of the equipment is more likely to occur, and there is a possibility that the inspection could not be efficiently performed.

SUMMARY OF THE INVENTION

The disclosure describes a substrate imaging apparatus achieving reduction in size and decrease in cost, while avoiding equipment failure.

A substrate imaging apparatus according to one aspect of the disclosure comprises: a rotary holding unit that holds and rotates a substrate; a mirror member having a reflecting surface that opposes an end face of the substrate and a peripheral portion of a back surface of the substrate held by the rotary holding unit, the reflecting surface being inclined with respect to a rotation axis of the rotary holding unit; and a camera having an imaging device that receives both first light and second light through a lens, the first light coming from a peripheral portion of a front surface of the substrate held by the rotary holding unit, and the second light being a reflected light of second light which comes from the end face of the substrate held by the rotary holding unit and is reflected by the reflecting surface.

In the substrate imaging apparatus according to the one aspect of the disclosure, the mirror member has the reflecting surface that opposes an end face of the substrate and a peripheral portion of a back surface of the substrate held by the rotary holding unit, the reflecting surface being inclined with respect to a rotation axis of the rotary holding unit. In addition, in the substrate imaging apparatus according to the one aspect of the disclosure, the imaging device receives both the first light and the second light through the lens, the first light coming from the peripheral portion of the front surface of the substrate held by the rotary holding unit, the second light being a reflected light of second light which comes from the end face of the substrate held by the rotary holding unit and is reflected by the reflecting surface. Thus, both the peripheral portion of the front surface of the substrate and the end face of the substrate are simultaneously imaged by the one camera. Thus, since plural cameras are no longer necessary, the space for installation of these cameras is no longer needed. In addition, since a mechanism for moving the camera is unnecessary, the space for installation of such a mechanism is not necessary. Namely, the substrate imaging apparatus according to the one aspect of the disclosure can have a significantly simplified structure. As a result, the substrate imaging apparatus can achieve reduction in size and decrease in cost, while avoiding equipment failure.

The reflecting surface may be a curved surface that is recessed away from the end face of the substrate held by the rotary holding unit. In this case, the size of a mirrored image of the end face of the substrate reflected on the reflecting surface is enlarged. Thus, a more detailed image of the end face of the substrate can be obtained. As a result, by processing the image, the end face of the substrate can be more precisely inspected.

The substrate imaging apparatus according to the one aspect of the disclosure may further comprise a focus adjusting lens disposed in an optical path of the second light extending from the reflecting surface to the lens in order to adjust an image forming position, at which an image of the end face of the substrate is formed, onto the imaging device. As compared with the length of the optical path of the first light extending to the lens, the length of the optical path of the second light extending from the reflecting surface to the lens is longer because of the length of the second light reflected by the mirror member. However, in this case, since the image forming position of the end face of the substrate can be adjusted by the focus adjusting lens onto the imaging device, the images of the peripheral portion of the front surface of the substrate and the end face of the substrate are both clear. As a result, by processing the image thus taken according to the above, the end face of the substrate can be more precisely inspected.

The substrate imaging apparatus according to the one aspect of the disclosure may further comprise an illuminating unit including a light source and a light diffusing member that diffuses light from the light source toward a first direction perpendicular to an optical axis of the light from the light source in order to generate diffused light, wherein the illuminating unit irradiates the peripheral portion of the front surface of the substrate held by the rotary holding unit with the diffused light, and irradiates the reflecting surface of the mirror member with the diffused light in order to allow the diffused light reflected by the mirror member to fall on the end surface of the substrate held by the rotary holding unit. In this case, since the light from light source is diffused toward the first direction, the diffused light enters the end face of the substrate from various directions. Thus, the entire end face of the substrate can be uniformly illuminated. As a result, the end face of the substrate can be more clearly imaged.

The illuminating unit may further include: a light scattering member that scatters the light form the light source to generate scattered light; and a cylindrical lens that allows the scattered light from the light scattering member to pass through the light diffusing member, the cylindrical lens being convex toward the light diffusing member, wherein the cylindrical lens diffuses light coming into the cylindrical lens toward a second direction perpendicular to an optical axis of the light emitted from the light source and perpendicular to the first direction. In this case, since the scattered light is diffused toward the first and second directions, the diffused light enters the end face of the substrate from various directions. Thus, the end face of the substrate can be uniformly illuminated. As a result, the entire end face of the substrate can be more clearly imaged.

The substrate imaging apparatus according to the disclosure can achieve reduction in size and decrease in cost, while avoiding equipment failure.

DESCRIPTION OF EMBODIMENTS

It should be firstly noted that the present invention is not limited to the below-described illustrative embodiments. In the below-described description, the same element or an element having the same function are designated by the same reference symbol, and overlapping description is omitted.

<Substrate Processing System>

Figure 1:
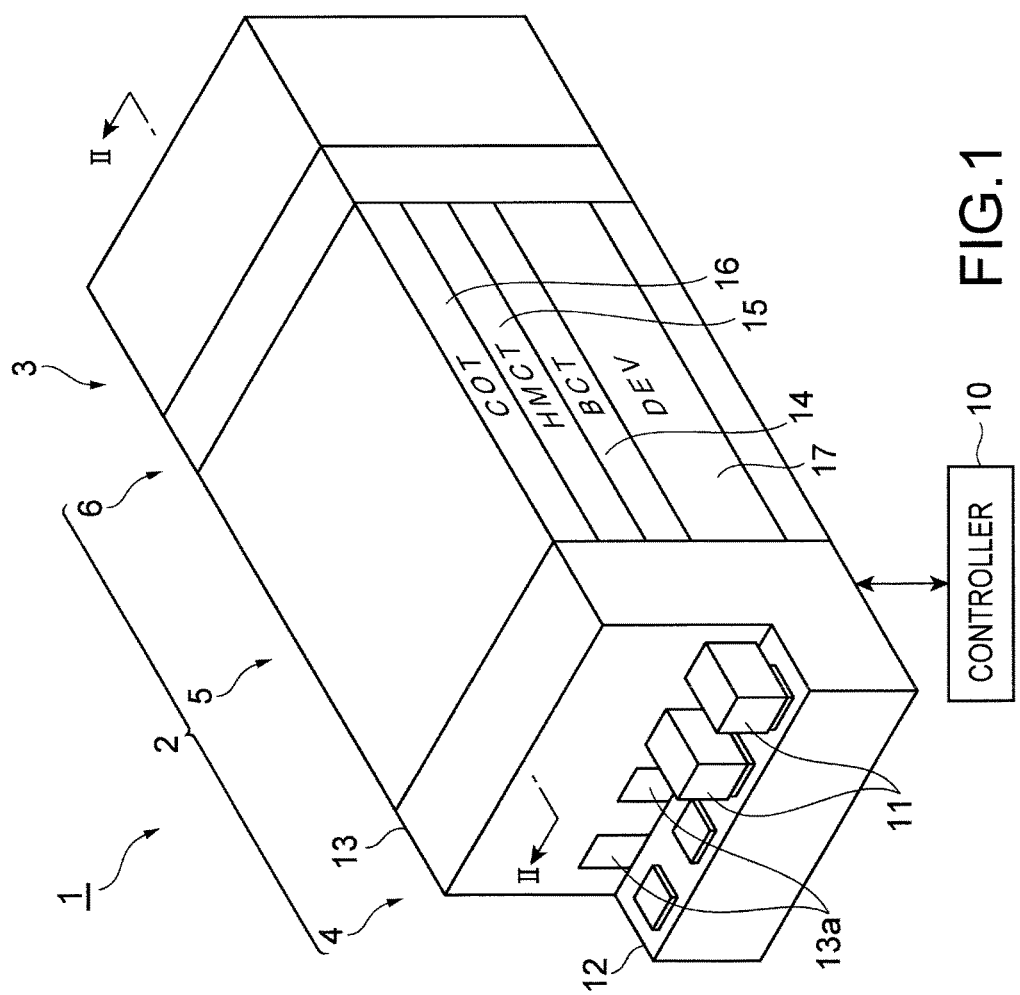
FIG. 1 is a perspective view showing a substrate processing system.

As shown in FIG. 1, a substrate processing system 1 (substrate processing apparatus) includes a coating and developing apparatus 2 (substrate processing apparatus) and a controller 10 (control unit). The substrate processing system 1 is equipped with an exposure apparatus 3. The exposure apparatus 3 has a controller (not shown) capable of communicating with the controller 10 of the substrate processing system 1. The exposure apparatus 3 is configured to send and receive a wafer W (substrate) to and from the coating and developing apparatus 2, and to perform an exposure process (pattern exposure) of a photosensitive resist film formed on a front surface Wa of a wafer W (see FIG. 10). To be specific, a part to be exposed of the photosensitive resist film (photosensitive coating film) is selectively irradiated with an energy beam (ray) using a suitable method such as liquid immersion exposure. The energy beam may be, for example, ArF excimer laser, KrF excimer laser, g-ray, i-ray or EUV (Extreme Ultraviolet) ray.

Before the exposure process by the exposure apparatus 3, the coating and developing apparatus 2 performs a process for forming a photosensitive resist film or a non-photosensitive resist film (collectively referred to as "resist film" herebelow) on the front surface Wa of the wafer W. After the exposure process by the exposure apparatus 3, the coating and developing apparatus 2 performs a process for developing the exposed photosensitive resist film.

The wafer W may have a circular plate shape or may have a plate shape other than the circular shape such as a polygonal shape. The wafer W may have a cutout formed by partially cutting out the wafer W. The cutout may be, for example, a notch (U-shape or V-shaped groove) or a linearly extending part (so-called orientation flat). The wafer W may be, for example, a semiconductor substrate, a glass substrate, a mask substrate, an FPD (Flat Panel Display) substrate, or other various substrates. A diameter of the wafer W may be, for example, about 200 mm to 450 mm. When an edge of the wafer W is beveled (chamfered), the "front surface" in this specification includes the beveled part when seen from the side of the front surface Wa of the wafer W. Similarly, a "back surface" in this specification includes a beveled part when seen from the side of a back surface Wb of the wafer W (see FIG. 10). An "end face" in this specification includes a beveled part when seen from the side of an end face We of the wafer W (see FIG. 10).

Figure 2:
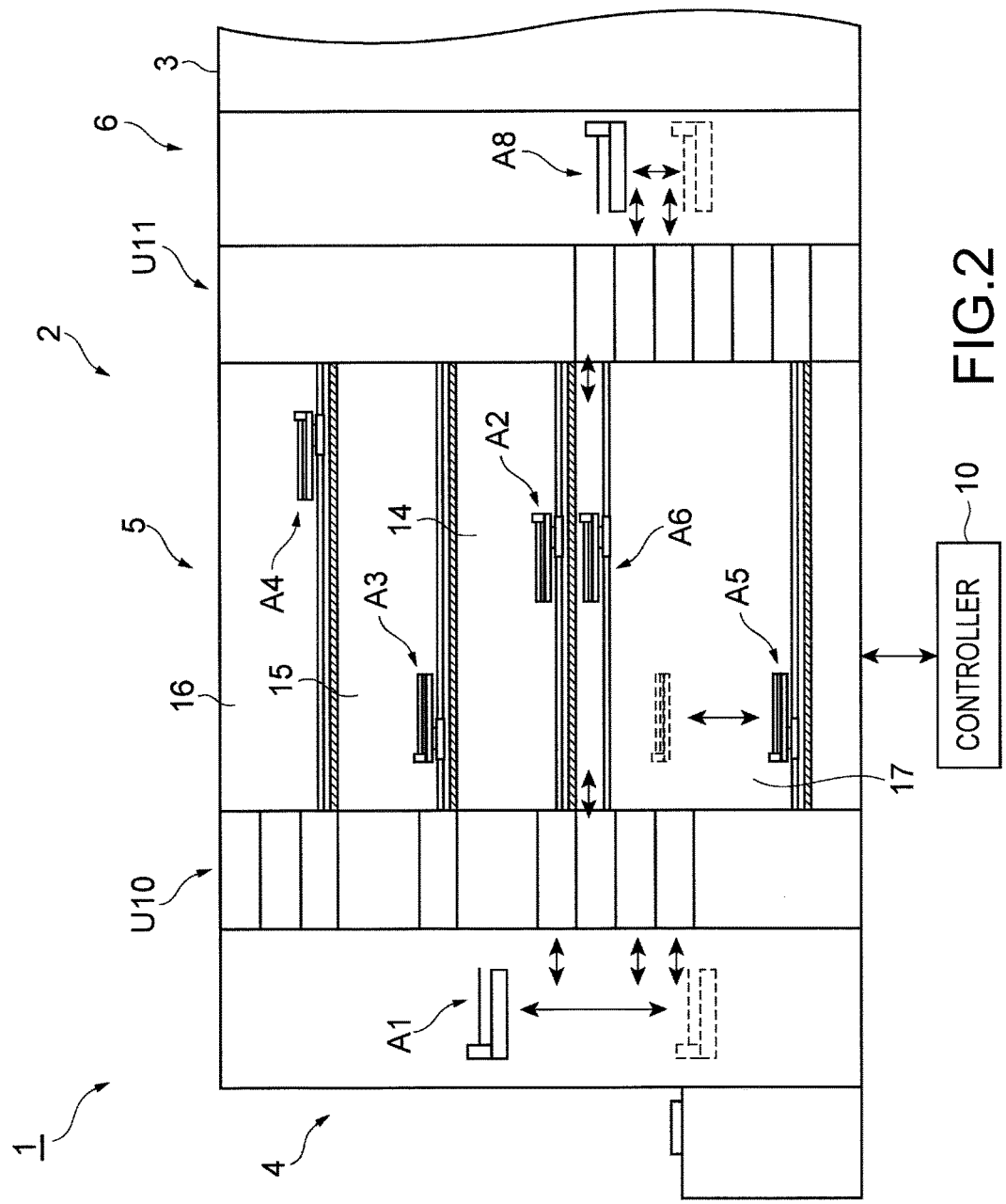
FIG. 2 is a sectional view taken along the II-II line in FIG. 1.
Figure 3:
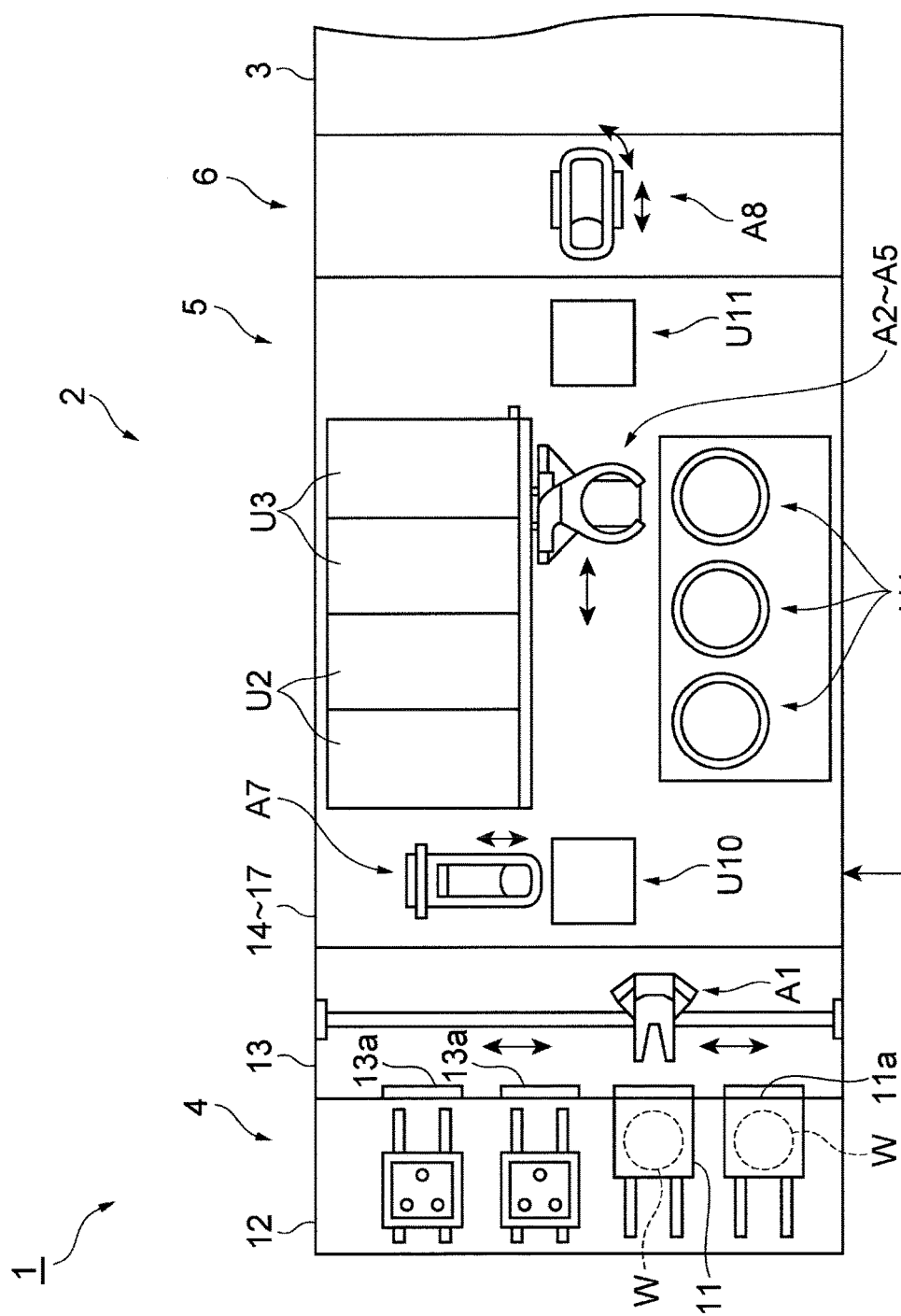
FIG. 3 is a plan view showing unit processing blocks (BCT block, HMCT block, COT block and DEV block).

As shown in FIGS. 1 to 3, the coating and developing apparatus 2 includes a carrier block 4, a processing block 5 and an interface block 6. The carrier block 4, the processing block 5 and the interface block 6 are arrayed horizontally.

As shown in FIGS. 1 and 3, the carrier block 4 includes a carrier station 12 and a loading and unloading unit 13. The carrier station 12 supports thereon a plurality of carriers 11. Each carrier 11 can sealingly contain at least one wafer W. A side surface 11a of the carrier 11 is provided with an opening and closing door (not shown) through which a wafer W is taken into and out from the carrier 11. The carrier 11 is detachably installed on the carrier station 12 such that the side surface 11a faces the loading and unloading unit 13.

The loading and unloading unit 13 is positioned between the carrier station 12 and the processing block 5. The loading and unloading unit 13 has a plurality of opening and closing door 13a. When the carrier 11 is placed on the carrier station 12, the opening and closing door of the carrier 11 faces the opening and closing door 13a. By simultaneously opening the opening and closing door 13a and the opening and closing door in the side surface 11a, the inside of the carrier 11 and the inside of the loading and unloading unit 13 communicate with each other. The loading and unloading unit 13 incorporates a delivery arm A1. The deliver arm A1 takes a wafer W out from the carrier 11 and delivers it to the processing block 5, as well as receives a wafer W from the processing block 5 and returns it into the carrier 11.

As shown in FIGS. 1 and 2, the processing block 5 has unit processing blocks 14 to 17. The unit processing blocks 14 to 17 are arranged such that the unit processing block 17, the unit processing block 14, the unit processing block 15 and the unit processing block 16 are aligned in this order from the floor surface side. As shown in FIG. 3, each of the unit processing blocks 14 to 17 has a liquid processing unit U1, a thermal processing unit U2 and an inspection unit U3.

The liquid processing unit U1 is configured to supply various process liquids to a front surface Wa of a wafer W. The thermal processing unit U2 is configured to perform a thermal process by heating a wafer W by, e.g., a heat plate and cooling the heated wafer W by, e.g., a cooling plate. The inspection unit U3 is configured to inspect respective surfaces (front surface Wa, back surface Wb and end face Wc) of a wafer W (which will be described in detail later).

The unit processing block 14 is a lower film forming block (BCT block) configured to form a lower film on a front surface Wa of a wafer W. The unit processing block 14 incorporates a transfer arm A2 that transfers a wafer W to the respective units U1 to U3 (see FIG. 2). The liquid processing unit U1 of the unit processing block 14 forms a coating film by coating a front surface Wa of a wafer W with a coating liquid for forming the lower film. The thermal processing unit U2 of the unit processing block 14 performs various thermal processes for forming the lower film. A concrete example of the thermal processes may be a heating process for hardening the coating film into the lower film. The lower film may be an antireflection (SiARC) film, for example.

The unit processing block 15 is an intermediate film (hard mask) forming block (HMCT block) configured to form an intermediate film on the lower film. The unit processing block 15 incorporates a transfer arm A3 that transports a wafer W to the respective units U1 to U3 (see FIG. 2). The liquid processing unit U1 of the unit processing block 15 forms a coating film by coating the lower film with a coating liquid for forming the intermediate film. The thermal processing unit U2 of the unit processing block 15 performs various thermal processes for forming the intermediate film. A concrete example of the thermal processes may be a heating process for hardening the coating film into the intermediate film. The intermediate film may be an SOC (Spin On Carbon) film or an amorphous carbon film, for example.

The unit processing block 16 is a resist film forming block (COT block) configured to form a thermosetting resist film on the intermediate film. The unit processing block 16 incorporates a transfer arm A4 that transfers a wafer W to the respective units U1 to U3 (FIG. 2). The liquid processing unit U1 of the unit processing block 16 forms a coating film by coating the intermediate film with a coating liquid (resist agent) for forming a resist film. The thermal processing unit U2 of the unit processing block 16 performs various thermal processes for forming the resist film. A concrete example of the thermal processes may be a heating process (PAB: Pre Applied Bake) for hardening the coating film into the resist film.

The unit processing block 17 is a developing block (DEV block) configured to develop an exposed resist film. The unit processing block 17 incorporates a transfer arm A5 that transfers a wafer W to the respective units U1 to U3, and a direct transfer arm A6 that transfers a wafer W without passing through these units (see FIG. 2). The liquid processing unit U1 of the unit processing block 17 develops the exposed resist film by supplying a developer to the resist film. The liquid processing unit U1 of the unit processing block 17 supplies a rinse liquid to the developed resist film so as to rinse away dissolved components of the resist film together with the developer. Thus, the resist film is partly removed, so that a resist pattern is formed. The thermal processing unit U2 of the unit processing block 16 performs various thermal processes for the developing process. A concrete example of the thermal processes may be a heating process before the developing process (PEB: Post Exposure Bake), a heating process after the developing process (PB: Post Bake) and the like.

As shown in FIGS. 2 and 3, a shelf unit U10 is disposed in the processing block 5 on the side of the carrier block 4. The shelf unit U10 extends from the floor surface to the unit processing block 15, and is divided into a plurality of cells aligned in the vertical direction. An elevation arm A7 is provided near the shelf unit U10. The elevation arm A7 moves a wafer W up and down among the cells of the shelf unit U10.

A shelf unit U11 is disposed in the processing block 5 on the side of the interface block 6. The shelf unit extends from the floor surface to an upper part of the unit processing block 17, and is divided into a plurality of cells aligned in the vertical direction.

The interface block 6 incorporates a delivery arm A8, and is connected to the exposure apparatus 3. The delivery arm A8 is configured to take a wafer W from the shelf unit U11 and deliver it to the exposure apparatus 3, and is configured to receive a wafer W from the exposure apparatus 3 and return it to the shelf unit U11.

The controller 10 controls the substrate processing system 1 partly or entirely. Details of the controller 10 will be described later. The controller 10 can send and receive a signal to and from the controller of the exposure apparatus 3. Due to the cooperation of the respective controllers, the substrate processing system 1 and the exposure apparatus 3 are controlled.

<Structure of Inspection Unit>

Figure 4:
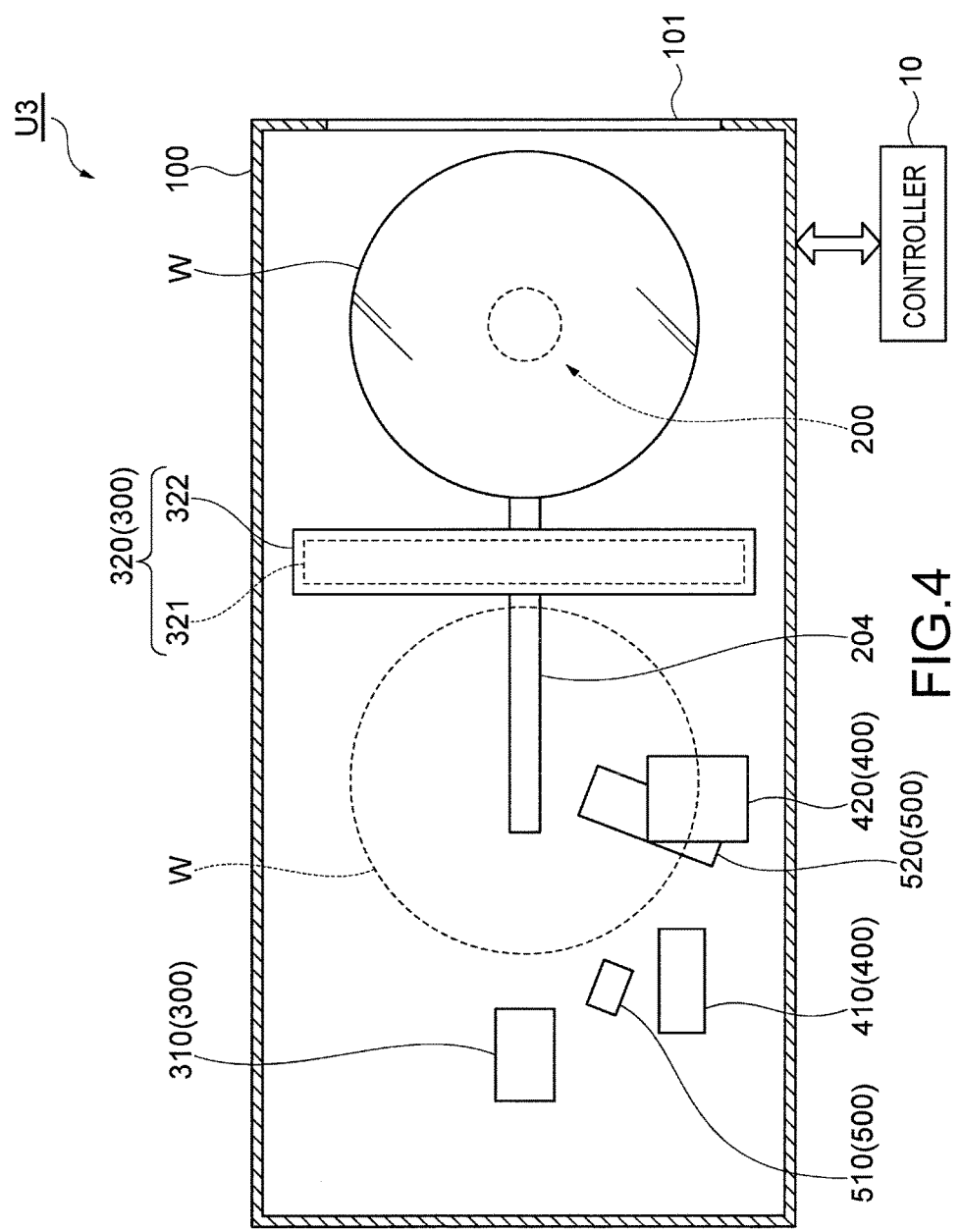
FIG. 4 is a sectional view of an inspection unit seen from above.
Figure 5:
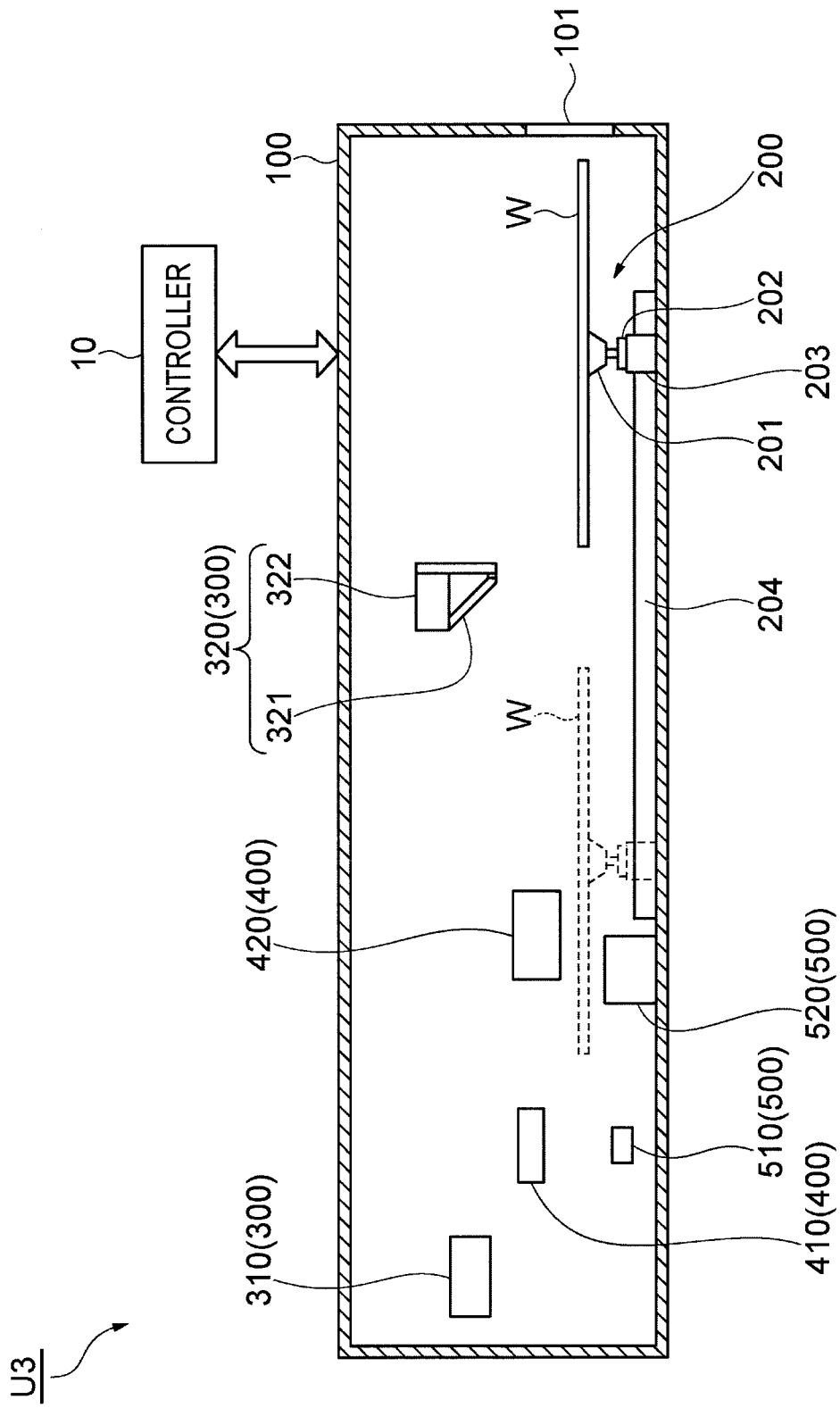
FIG. 5 is a sectional view of the inspection unit seen from the lateral side.
Figure 6:
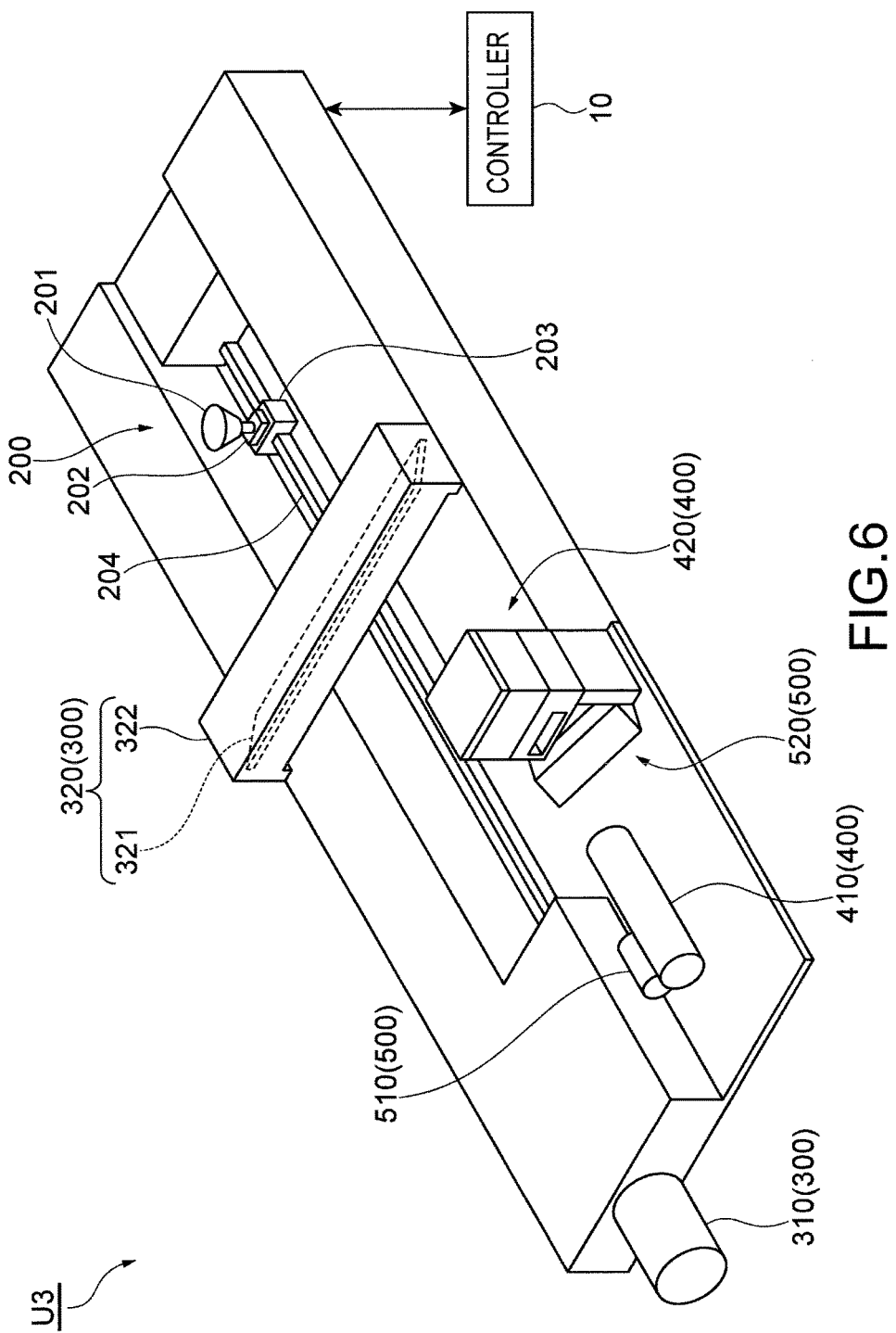
FIG. 6 is a perspective view showing the inspection unit.

Next, the inspection unit U3 is described in more detail with reference to FIGS. 4 to 20. As shown in FIGS. 4 to 6, the inspection unit U3 includes a housing 100, a rotary holding subunit 200 (rotary holding unit), a front surface imaging subunit 300, a periphery imaging subunit 400 (substrate imaging apparatus) and a back surface imaging subunit 500. The respective subunits 200 to 500 are accommodated in the housing 100. A loading and unloading port 101 is formed in one end wall of the housing 100, through which a wafer W is loaded to the inside of the housing 100 and unloaded to the outside of the housing 100.

The rotary holding subunit 200 includes a holding table 201, actuators 202, 203 and a guide rail 204. The holding table 201 is structured as a suction chuck that substantially horizontally holds a wafer W by suction, for example. The shape of the holding table 201 (suction chuck) is not limited, and may be circular, for example. The size of the holding table 201 may be smaller than a wafer W.

The actuator 202 is, e.g., an electric motor that drives the holding table 201 for rotation. Namely, the actuator 202 rotates a wafer W held on the holding table 201. The actuator 202 may include an encoder for detecting a rotating position of the holding table 201. In this case, positions of the respective surfaces of a wafer W to be imaged by the respective imaging subunits 300, 400, 500 and the rotating position can be related to each other. If a wafer W has a cutout, the posture of the wafer W can be specified based on the cutout recognized by the respective imaging subunits 300, 400, 500, and the rotating position detected by the encoder.

The actuator 203 is, e.g., a linear actuator that moves the holding table 201 along the guide rail 204. Namely, the actuator 203 allows a wafer W held on the holding table 201 to be transferred between one end and the other end of the guide rail 204. Thus, the wafer W held on the holding table 201 can be moved between a first position near the loading and unloading port 101, and a second position near the periphery imaging subunit 400 and the back surface imaging subunit 500. The guide rail 204 extends linearly (e.g., like a straight line) in the housing 100.

The front surface imaging subunit 300 includes a camera 310 (imaging means) and an illuminating module 320. The camera 310 and the illuminating module 320 constitute a set of imaging modules. The camera 310 includes a lens and one imaging device (e.g., CCD image sensor, CMOS image sensor, etc.). The camera 310 opposes the illuminating module 320 (illuminating unit).

The illuminating module 320 includes a half mirror 321 and a light source 322. The half mirror 321 is disposed in the housing 100 such that it is inclined at substantially 45° with respect to the horizontal direction. The half mirror 321 is located above an intermediate portion of the guide rail 204 such that the half mirror 321 intersects the guide rail 204 when viewed from above. The half mirror 321 has a rectangular shape. The length of the half mirror 321 is larger than the diameter of a wafer W.

The light source 322 is located above the half mirror 321. The light source 322 is longer than the half mirror 321. Light emitted from the light source 322 passes through the whole half mirror 321 to travel downward (toward the guide rail 204). The light having passed through the half mirror 321 is reflected by an object located below the half mirror 321, and is again reflected by the half mirror 321. The light passes through the lens of the camera 310 and enters the imaging device of the camera 310. Namely, the camera 310 can take an image of an object present in an irradiation area of the light source 322 through the half mirror 321. For example, when the holding table 201 holding a wafer W is moved by the actuator 203 along the guide rail 204, the camera 310 can take an image of the front surface Wa of the wafer W which passes through the irradiation area of the light source 322. Data of the image taken by the camera 310 is transmitted to the controller 10.

As shown in FIGS. 4 to 10, the periphery imaging subunit 400 includes a camera 410 (imaging means), an illuminating module 420 and a mirror member 430. The camera 410, the illuminating module 420 (illuminating unit) and the mirror member 430 constitute a set of imaging modules. The camera 410 includes a lens 411 and one imaging device 412 (e.g., CCD image sensor, CMOS image sensor, etc.). The camera 410 opposes the illuminating module 420.

Figure 10:
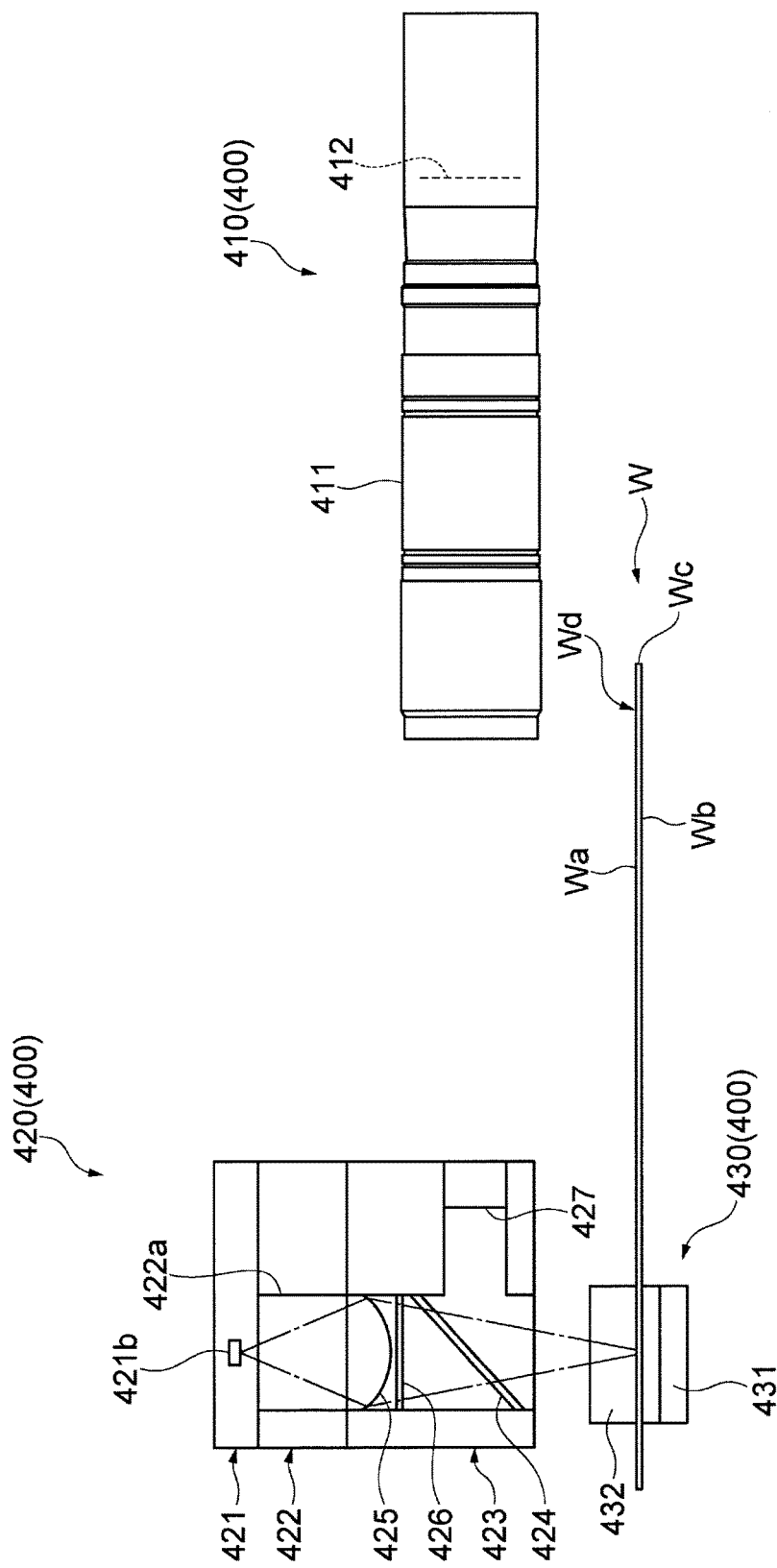
FIG. 10 is a side view of a two-face imaging module.
Figure 11:
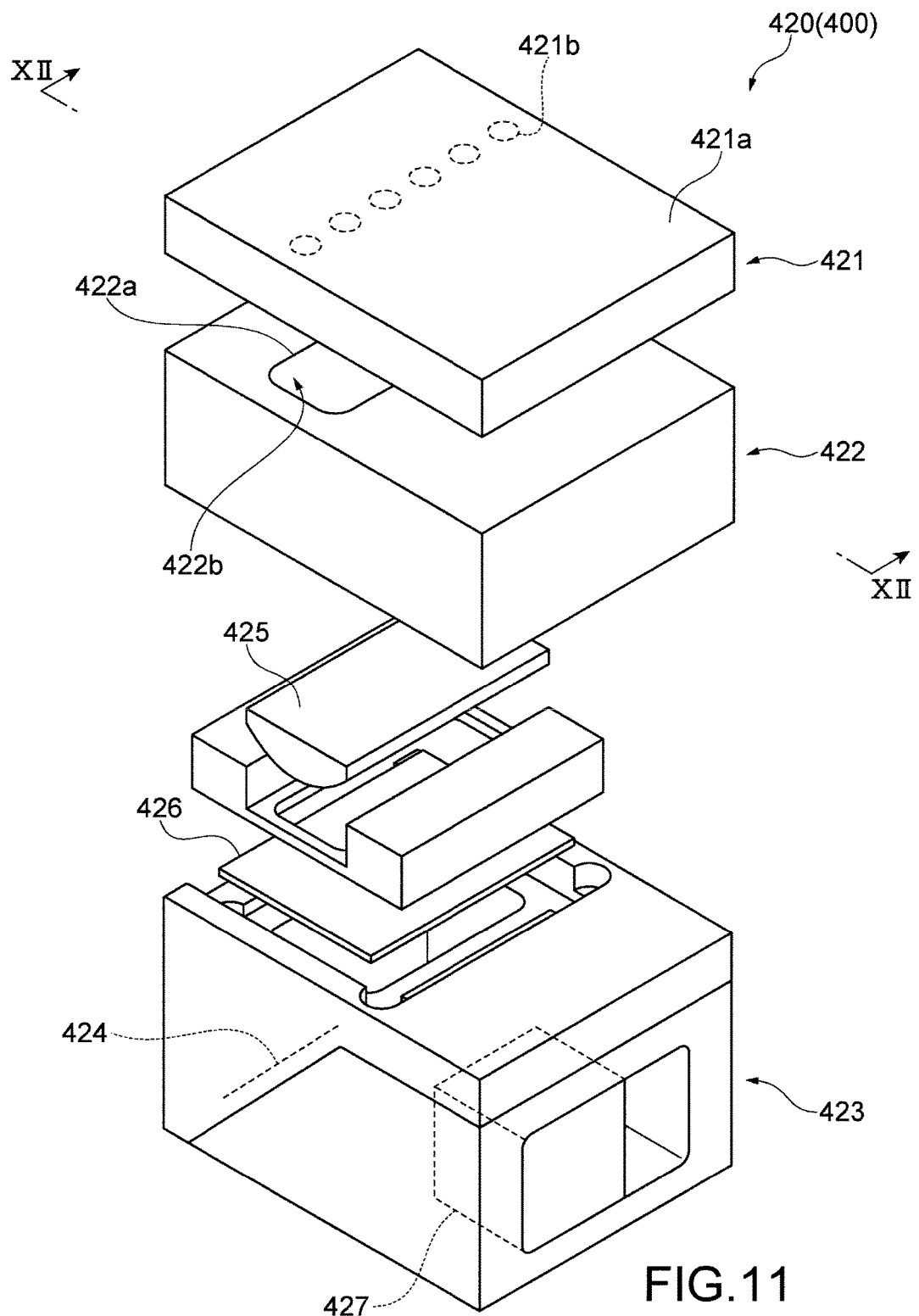
FIG. 11 is an exploded perspective view showing an illuminating module.
Figure 12:
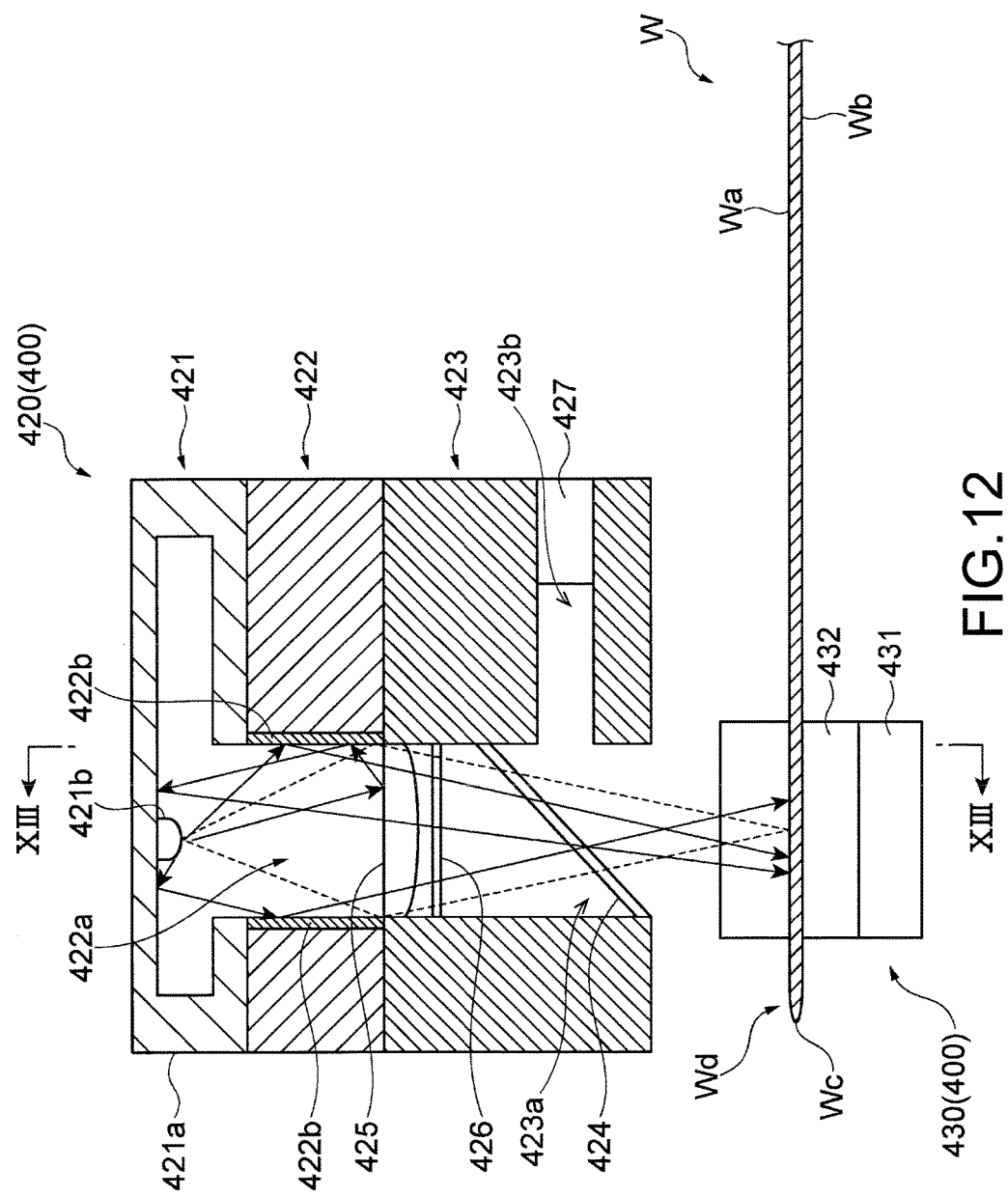
FIG. 12 is a sectional view taken along the XII-XII line in FIG. 11.
Figure 13:
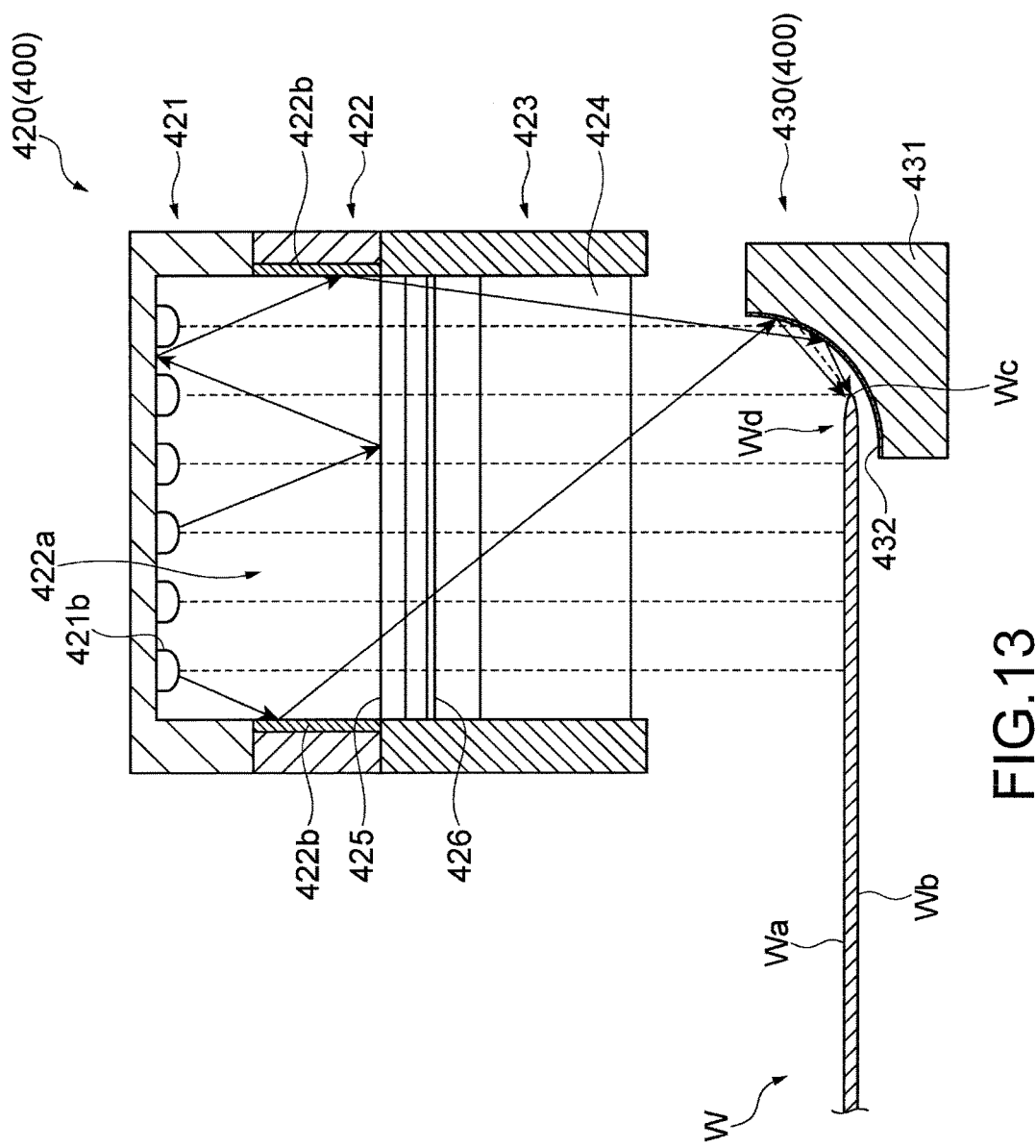
FIG. 13 is a sectional view taken along the XIII-XIII line in FIG. 11.
Figure 14A:
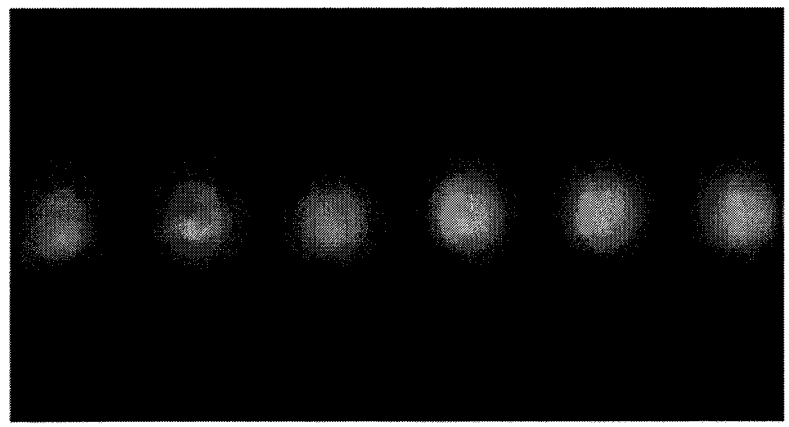
FIG. 14A is a picture showing a condition where light from a light source passed through a light scattering member.
Figure 14B:
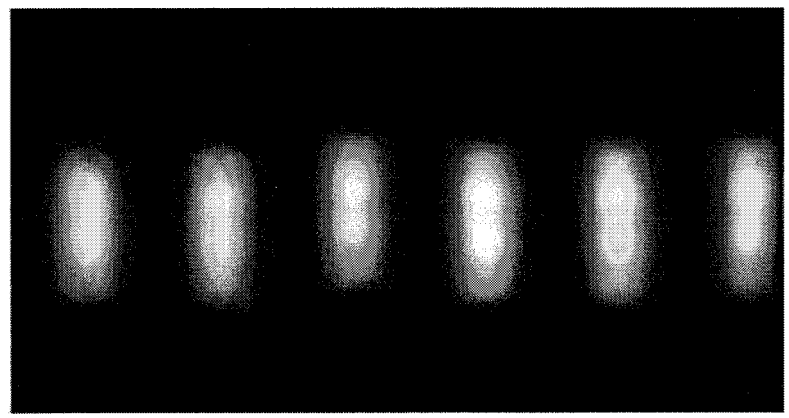
FIG. 14B is a picture showing a condition where the light from the light source passed through the light scattering member and the cylindrical lens.
Figure 14C:
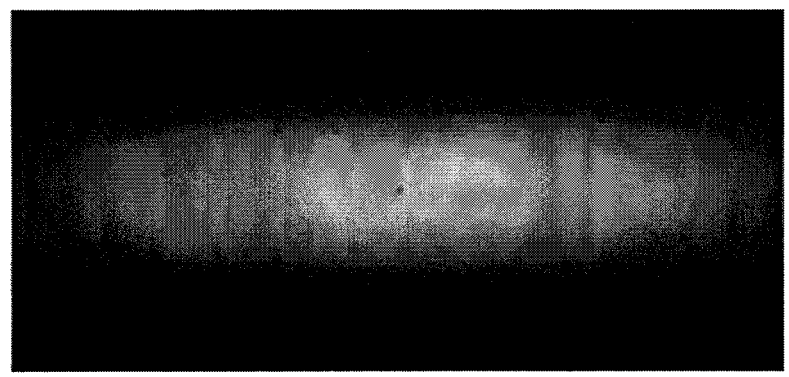
FIG. 14C is a picture showing a condition where the light from the light source passed through the light scattering member, the cylindrical lens and the light diffusing member.

As shown in FIGS. 7 to 13, the illuminating module 420 is located above the wafer W held on the holding table 201. The illuminating module 420 includes a light source 421, a light scattering member 422 and a holding member 423. As shown in FIGS. 11 to 13, the light source 421 is composed of, for example, a housing 421*a* and a plurality of LED point light sources 421*b* disposed in the housing 421*a*. These LED point light sources 421*b* are arranged in a line along the radial direction of the wafer W.

As shown in FIGS. 7 to 13, the light scattering member 422 is connected to the light source 421 so as to overlap with the light source 421. As shown in FIGS. 11 to 13, the light scattering member 422 has a through-hole 422*a* that extends along the direction in which the light source 421 and the light scattering member 422 overlap with each other. An inner wall surface of the through-hole 422*a* is mirror finished. For the mirror finish, the inner wall surface may be plated with electroless nickel so as to form a plating film 422*b*. Thus, when light from the light source 421 enters the through-hole 422*a* of the light scattering member 422, the incident light is irregularly reflected by the plating film 422b, as shown in FIGS. 12 and 13. Therefore, scattered light is generated in the light scattering member 422 (see FIG. 14A).

As shown in FIGS. 7 to 13, the holding member 423 is connected to the light scattering member 422 so as to overlap with the light scattering member 422. As shown in FIGS. 10 to 13, the holding member 423 has a through-hole 423a and an intersection hole 423b that intersects the through-hole 423a. The through-hole 423a extends along a direction in which the light scattering member 422 and the holding member 423 are overlapped with each other. The intersection hole 423b extends from one side surface of the holding member 423 toward the through-hole 423a along a direction perpendicular to the through-hole 423a. The intersection hole 423b is connected to the through-hole 423a.

As shown in FIGS. 7 to 13, the holding member 423 holds therein a half mirror 424, a cylindrical lens 425, a light diffusing member 426, and focus adjusting lens 427. As shown in FIGS. 10 and 12, the half mirror 424 is disposed on an intersection part of the through-hole 423a and the intersection hole 423b such that the half mirror 424 is inclined at substantially 45° with respect to the horizontal direction. The half mirror 424 has a rectangular shape.

As shown in FIGS. 10 to 13, the cylindrical lens 425 is disposed between the holding member 423 and the half mirror 424. As shown in FIGS. 10 to 12, the cylindrical lens 425 is a convex cylindrical lens that is convex toward the half mirror 424. An axis of the cylindrical lens 425 extends in a direction in which the plurality of LED point light sources 421b are aligned. When scattered light from the light scattering member 422 enters the cylindrical lens 425, the scattered light is enlarged along a circumferential direction of the cylindrical surface of the cylindrical lens 425 (see FIG. 14B).

As shown in FIGS. 10 to 13, the light diffusing member 426 is disposed between the cylindrical lens 425 and the half mirror 424. The light diffusing member 426 is a sheet-shaped member having a rectangular shape, and diffuses light having passed through the cylindrical lens 425. Thus, diffused light is generated by the light diffusing member 426 (see FIG. 14C). For example, the light diffusing member 426 may have an isotropic diffusing function for diffusing incident light toward all the directions of the surface of the light diffusing member 426, or may have an anisotropic diffusing function for diffusing incident light toward the axial direction of the cylindrical lens 425 (directions perpendicular to the circumferential direction of the cylindrical surface of the cylindrical lens 425).

As shown in FIGS. 7, 8, 11 and 12, the focus adjusting lens 427 is disposed in the intersection hole 423b. As long as the focus adjusting lens 427 is a lens having a function for varying a synthetic focal length with respect to the lens 411, the configuration of the focus adjusting lens 427 is not limited. The focus adjusting lens 427 may be a lens having a parallelepiped shape, for example.

Figure 15A:
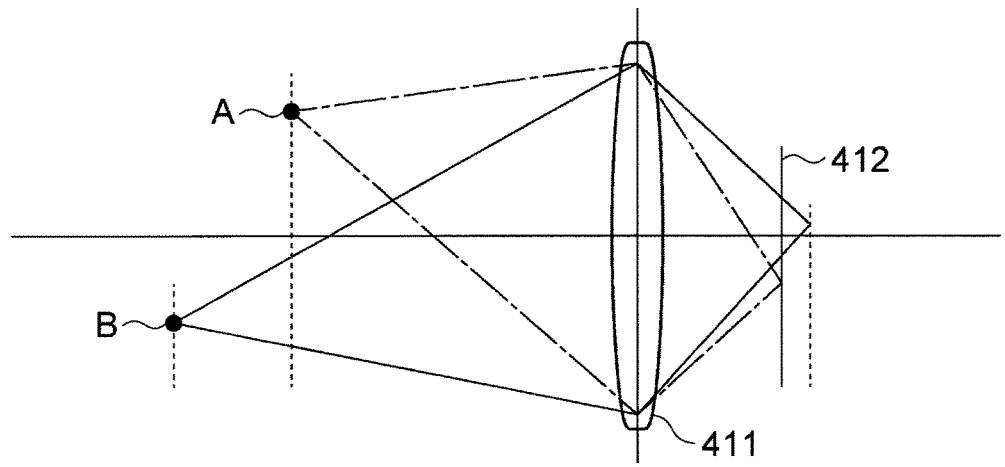
FIG. 15A is a diagram for explaining an optical path when there exists no focus adjusting lens.
Figure 15B:
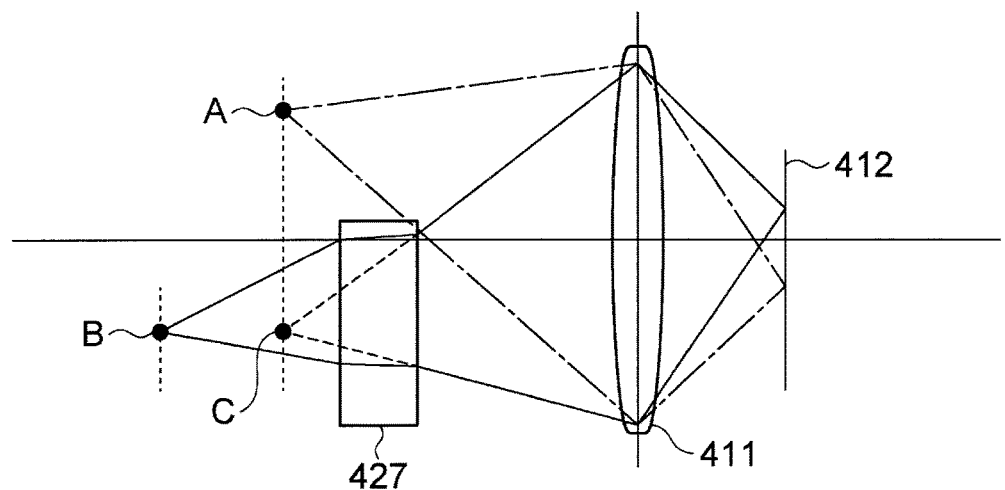
FIG. 15B is a diagram for explaining an optical path when there exists a focus adjusting lens.
Figure 16:
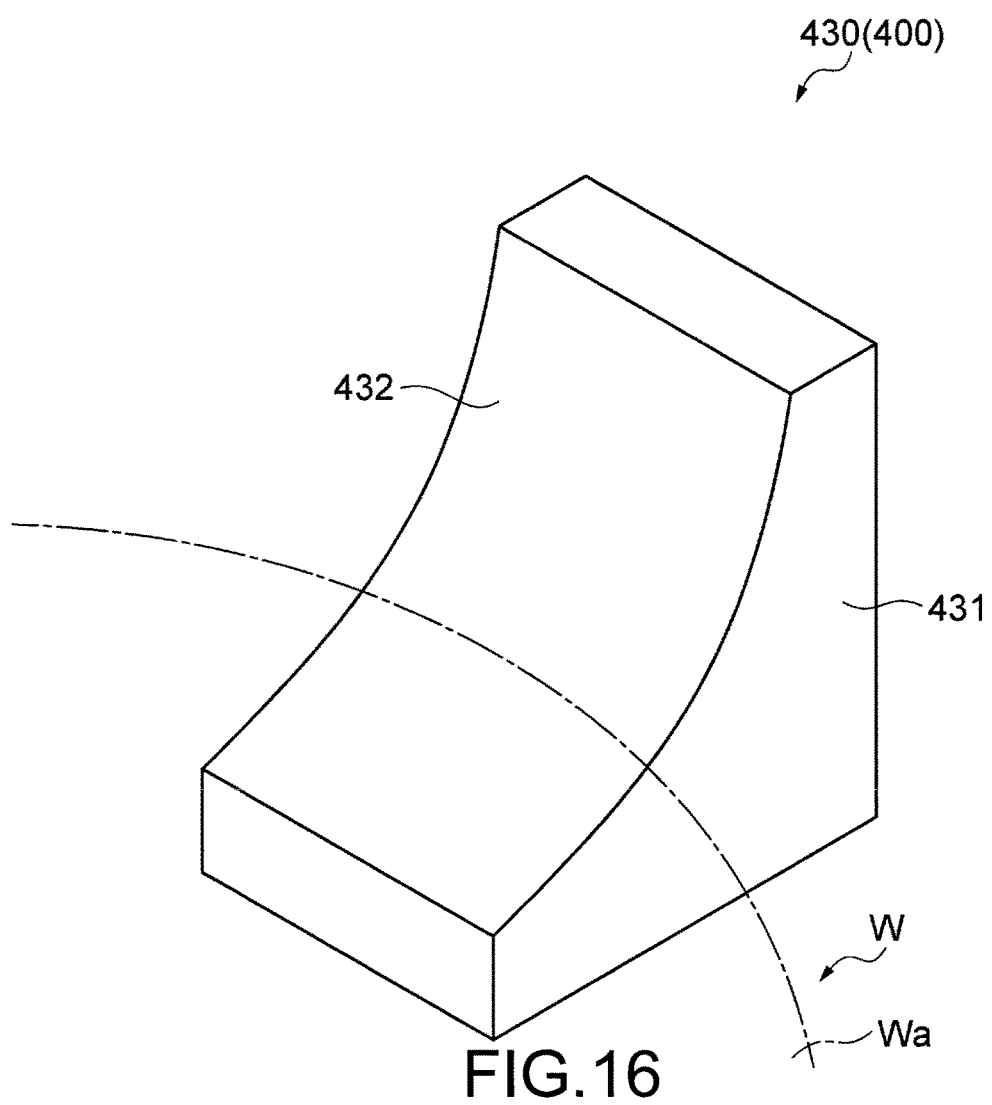
FIG. 16 is a perspective view of a mirror member.

Suppose that only the lens 411 is used. In this case, as shown in FIG. 15A, light from point A nearer to the lens 411 passes through the lens 411 and focuses on the imaging device 412, and light from point B farther from the lens 411 passes through the lens 411 and focuses on a point deviated from the imaging device 412 (behind the imaging device 412). Thus, the image of the point A taken by the imaging device 412 is clear (in focus), but the image of the point B taken by the imaging device 412 is likely to be unclear (out of focus). On the other hand, suppose that there is the focus adjusting lens 427. In this case, as shown in FIG. 15B, light from the point B farther from the lens 411 is refracted by the focus adjusting lens 427, and then the light passes through the lens 411 and focuses on the imaging device 412. Due to the existence of the focus adjusting lens 427, when the image of the point B is seen through the focus adjusting lens 427, the point B looks like as if the Point B was located at a C point coplanar with the point A. Thus, when seen from the lens 411, the distance between the point A and the lens 411, and a distance between the seeming position of the Point B (C point position) and the lens 411 are identical to each other. Accordingly, the light from the point A and the light from the Point B both focus on the imaging device 412. As a result, the images of the point A and the point B taken by the imaging device 412 are both clear. The above explanation similarly applies also to a case in which the focus adjusting lens 427 is a bifocal lens which has two portions with different refractive powers.

As shown in FIGS. 7, 10, 12, 13 and 16, the mirror member 430 is disposed below the illuminating module 420. As shown in FIGS. 7, 10, 12, 13, 16 and 17, the mirror member 430 includes a body 431 and a reflecting surface 432. The body 431 is made of an aluminum block.

Figure 7:
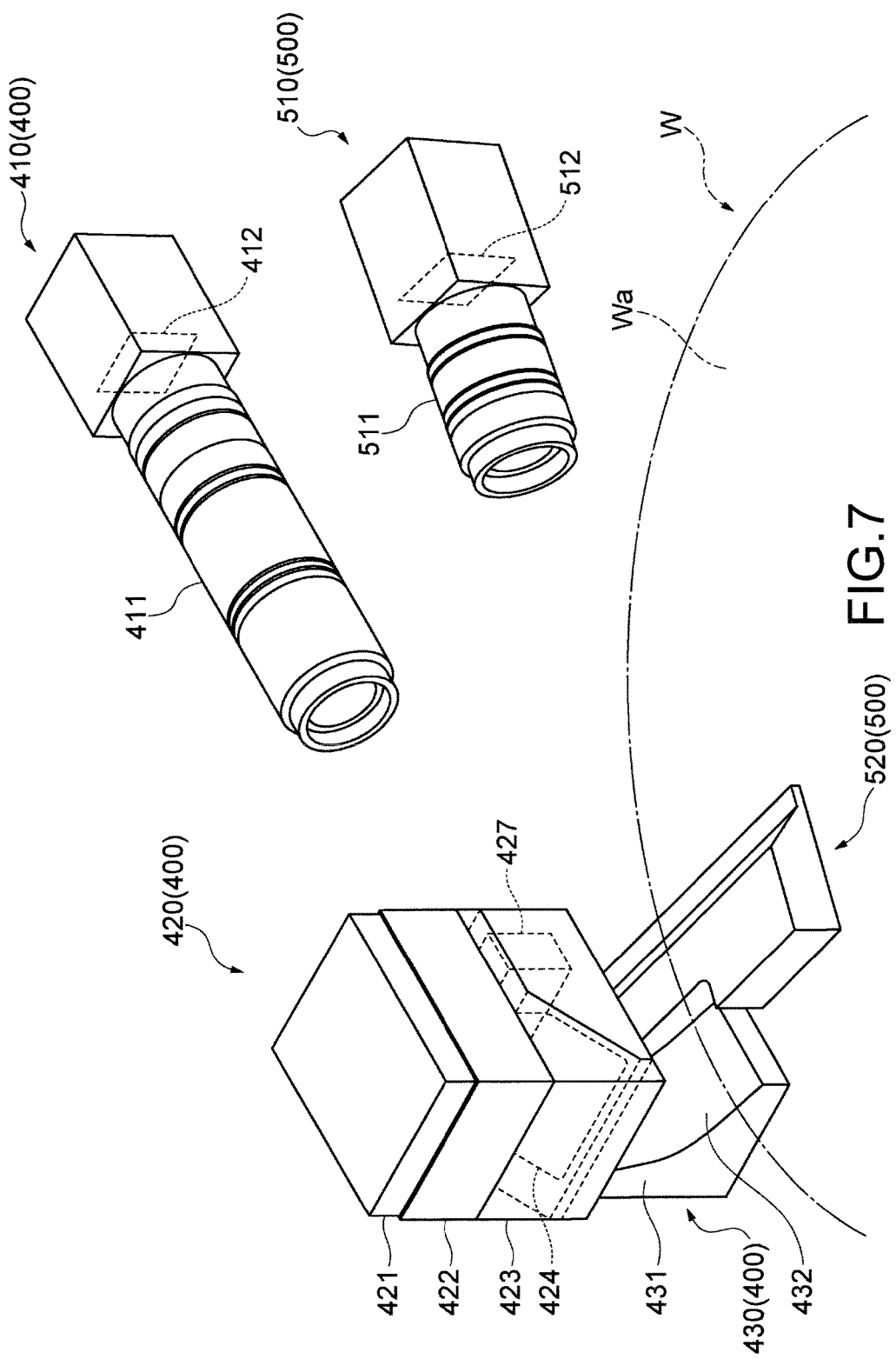
FIG. 7 is a perspective view of a periphery imaging subunit seen from the front side.
Figure 8:
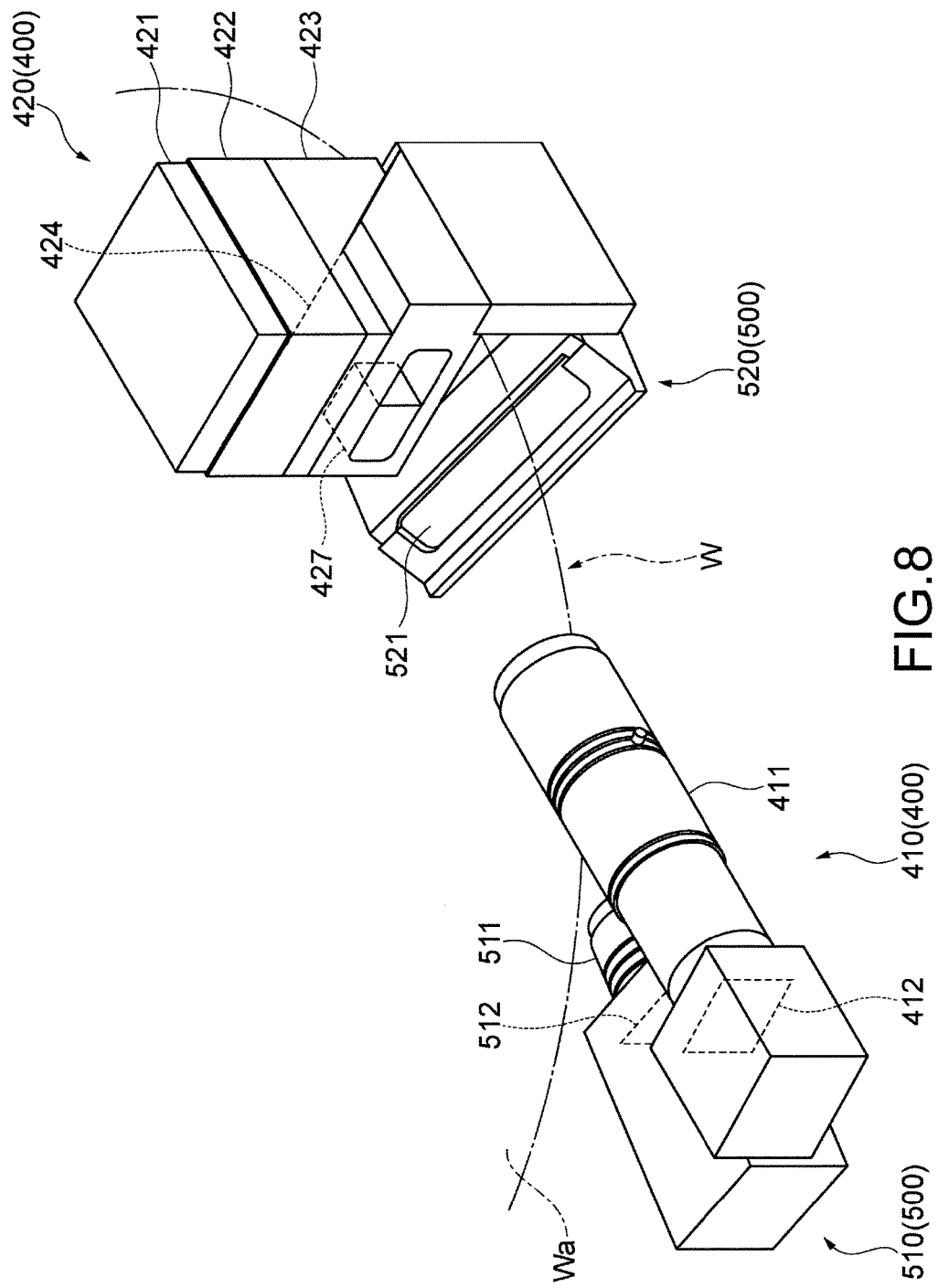
FIG. 8 is a perspective view of the periphery imaging subunit seen from behind.
Figure 9:
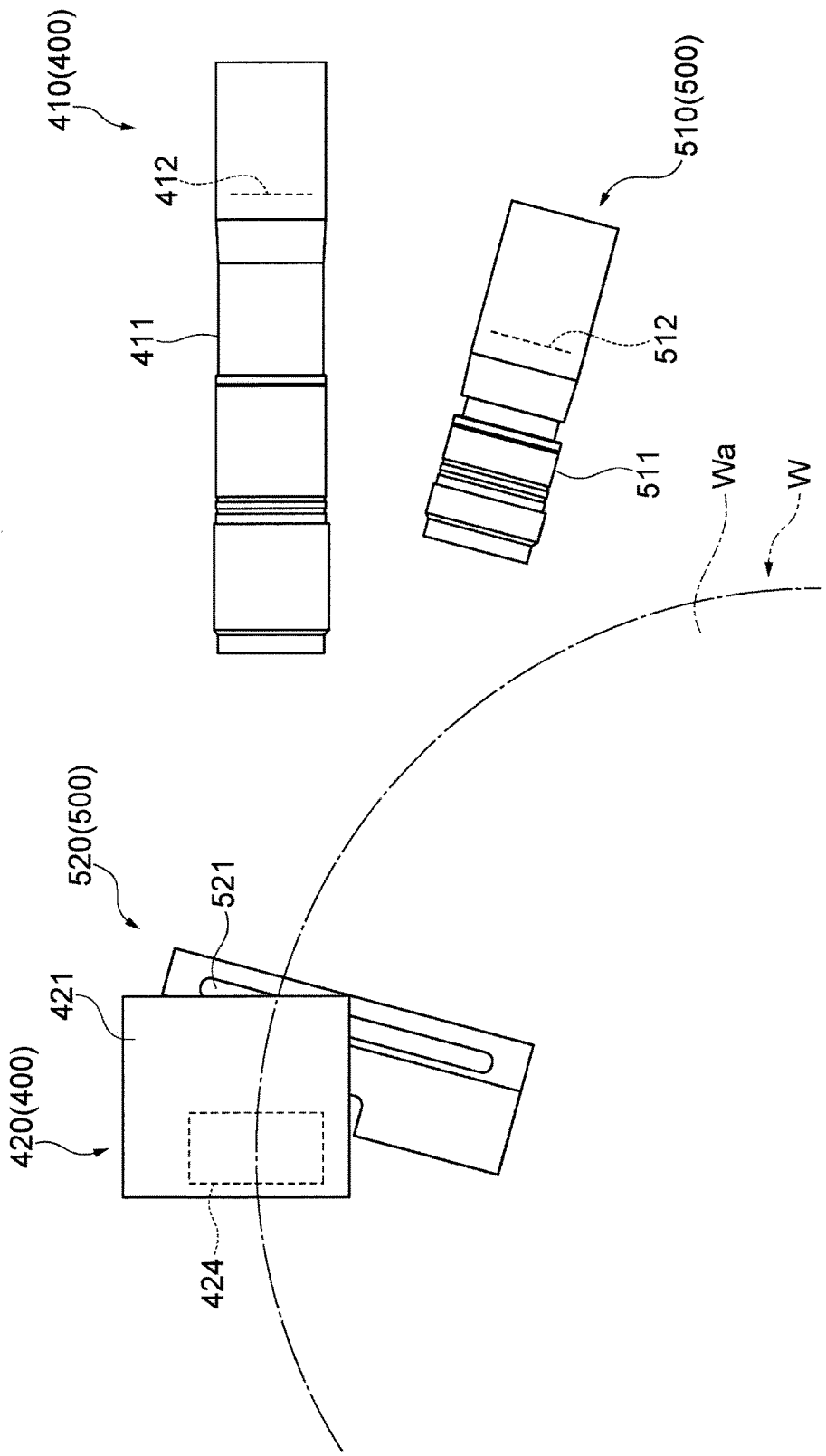
FIG. 9 is a plan view of the periphery imaging subunit.
Figure 17:
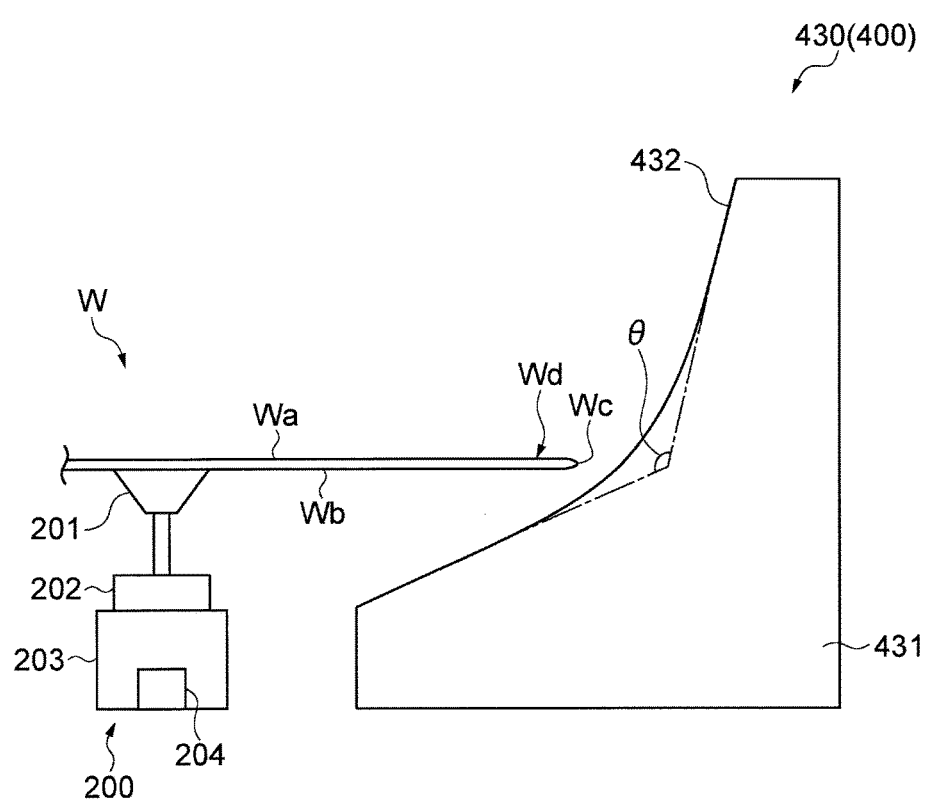
FIG. 17 is a side view of the mirror member.

As shown in FIGS. 7, 13 and 17, when a wafer W held by the holding table 201 is located at the second position, the reflecting surface 432 opposes an end face We of the wafer W and a peripheral portion Wd of a back surface Wb of the wafer W. The reflecting surface 432 is inclined with respect to the rotary axis of the holding table 201. The reflecting surface 432 is mirror finished. For example, a mirror sheet may be attached to the reflecting surface 432. Alternatively, an aluminum plating may be provided to the reflecting surface 432, or an aluminum material may be vapor-deposited on the reflecting surface 432.

The reflecting surface 432 is a curved surface that is recessed away from the end face Wc of the wafer W held on the holding table 201. Namely, the mirror member 430 is a concave mirror. Thus, a mirror image of the end face Wc of the wafer W reflected on the reflecting surface 432 is enlarged. A radius of curvature of the reflecting surface 432 may be about 10 mm to 30 mm, for example. A divergence angle θ (see FIG. 17) of the reflecting surface 432 may be about 100° to 150°. The divergence angle θ of the reflecting surface 432 herein means an angle defined by two planes circumscribing the reflecting surface 432.

Figure 18A:
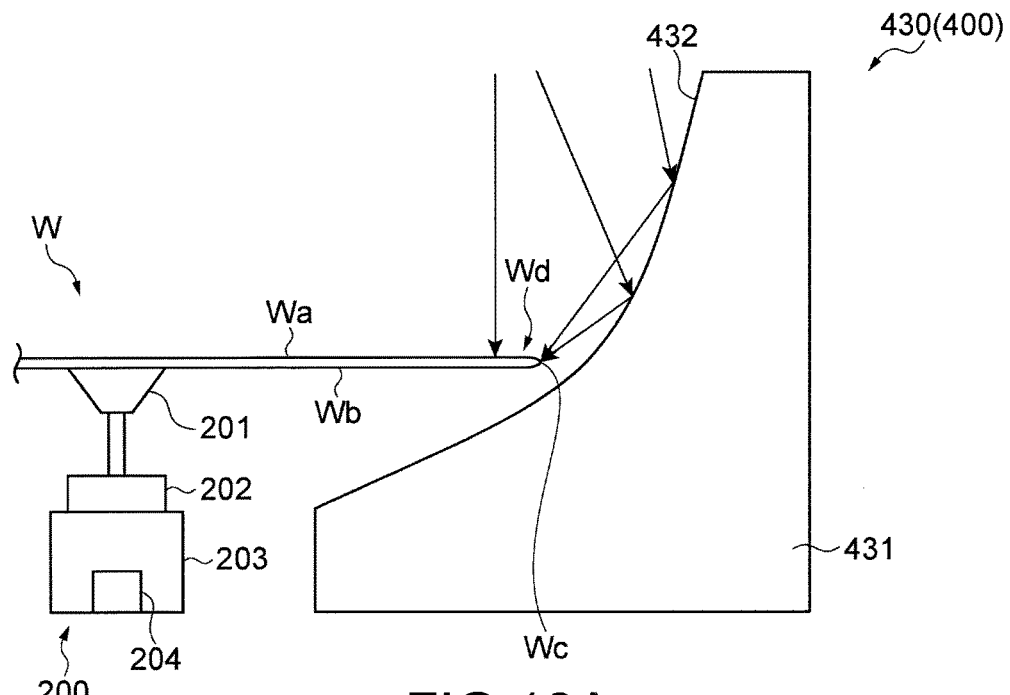
FIG. 18A is a diagram for explaining a condition where light from the illuminating module is reflected by the mirror member.

In the illuminating module 420, light emitted from the light source 421 is scattered by the light scattering member 422, enlarged by the cylindrical lens 425, and diffused by the light diffusing member 426. Thereafter, the light passes through the whole half mirror 424 to travel downward. The diffused light having passed through the half mirror 424 is reflected by the reflecting surface 432 of the mirror member 430 located below the half mirror 424. When a wafer W held on the holding table 201 is located at the second position as shown in FIGS. 13 and 18A, the diffused light having been reflected by the reflecting surface 432 mainly reaches the end face Wc of the wafer W (if the periphery of the wafer W has a beveled part, particularly an upper end of the beveled part) and the peripheral portion Wd of the front surface Wa.

Figure 18B:
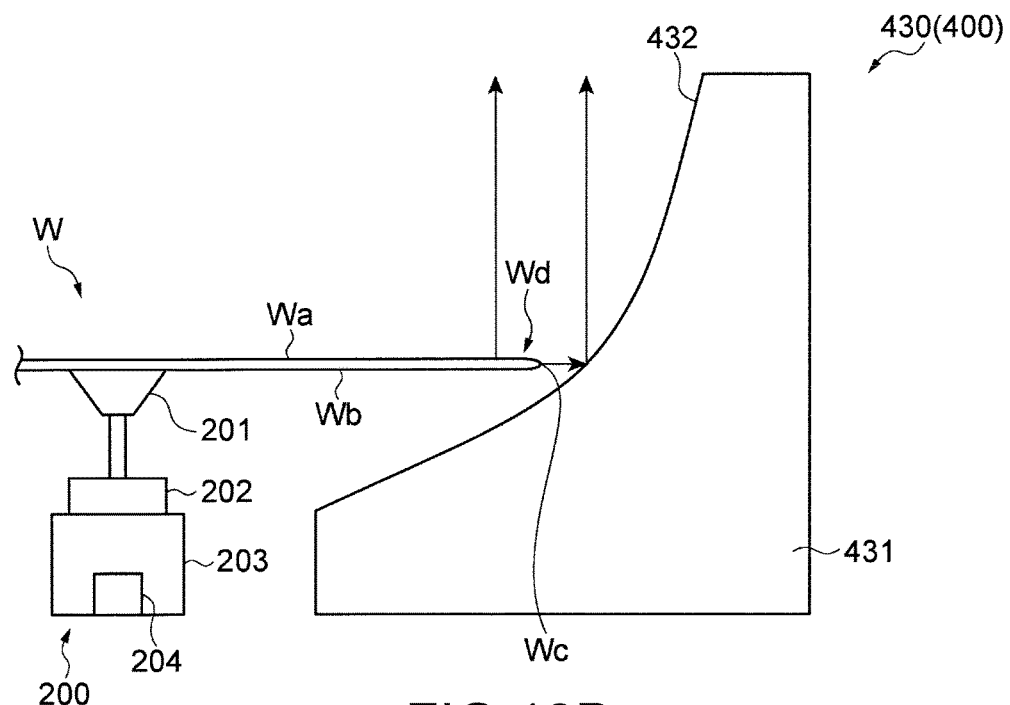
FIG. 18B is a diagram for explaining a condition where light from a wafer is reflected by the mirror member.
Figure 19A:
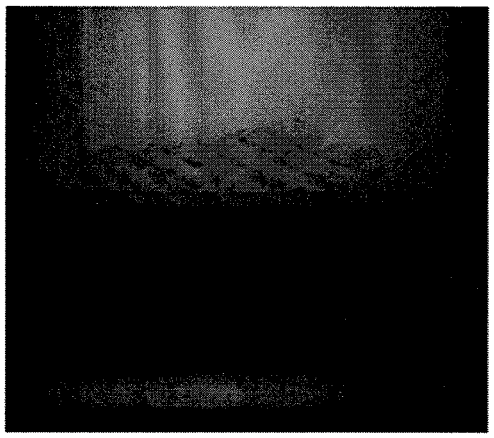
FIG. 19A shows an image that is taken when a front surface of a wafer is in focus without using focus adjusting lens.
Figure 19B:
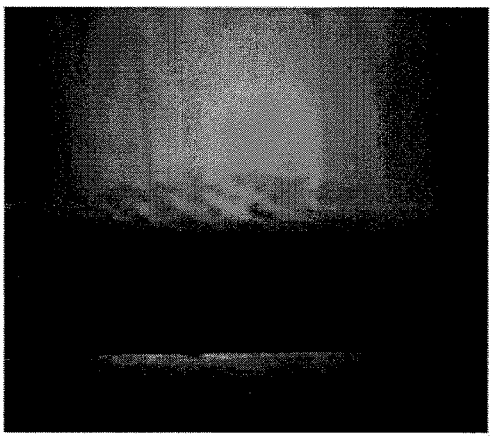
FIG. 19B shows an image that is taken when an end face of the wafer is in focus without using focus adjusting lens.
Figure 19C:
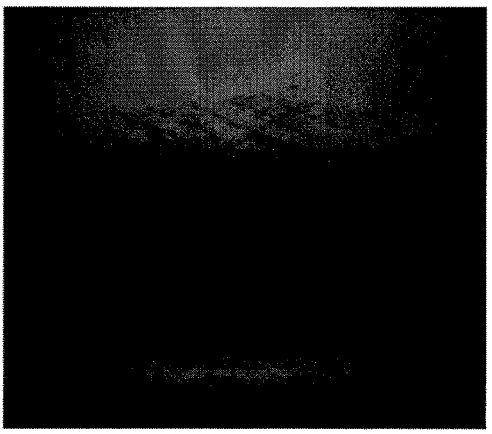
FIG. 19C shows an image that is taken when both of the front surface of the wafer and the end face are in focus with the use of the focus adjusting lens.

The light having been reflected from the peripheral portion Wd of the front surface Wa of the wafer W is not directed toward the reflecting surface 432 of the mirror member 430 but is reflected again by the half mirror 424 (see FIG. 18B). The light then passes through the lens 411 of the camera 410 to enter the imaging device 412 of the camera 410, without passing through the focus adjusting lens 427. On the other hand, the light having been reflected from the end face Wc of the wafer W is reflected sequentially by the reflecting surface 432 of the mirror member 430 and the half mirror 424. The light then passes sequentially through the focus adjusting lens 427 and the lens 411 of the camera 410 to enter the imaging device 412 of the camera 410. Thus, the optical path length of the light coming from the end face Wc of the wafer W to fall on the imaging device 412 of the camera 410 is longer than the optical path length of the light coming from the peripheral portion Wd of the front surface Wa of the wafer W to fall on the imaging device 412 of the camera 410. The optical path difference between these optical paths may be about 1 mm to 10 mm, for example. Thus, the imaging device 412 of the camera 410 receives both the light which comes from the peripheral portion Wd of the front surface Wa of the wafer W and the light which comes from the end face Wc of the wafer W. Namely, when the wafer W held by the holding table 201 is located at the second position, the camera 410 can image both the peripheral portion Wd of the front surface Wa of the wafer W and the end face Wc of the wafer W. Data of the images taken by the camera 410 are transmitted to the controller 10.

If the peripheral portion Wd of the front surface Wa of the wafer W is focused without the existence of the focus adjusting lens 427, the image of the peripheral portion Wd of the front surface Wa of the wafer W, which is taken by the camera 410, is clear, but the image of the end face Wc of the wafer W, which is taken by the camera 410, is likely to be unclear (see FIG. 19A), because of the optical path difference. On the other hand, if the end face of the wafer W is focused without the existence of the focus adjusting lens 427, the image of the end face Wc of the wafer W is clear, but the image of the peripheral portion Wd of the front surface Wa of the wafer W imaged by the camera 410 is likely to be unclear (see FIG. 19B), because of the optical path difference. However, since there actually exists the focus adjusting lens 427 in the optical path of the light extending from the reflecting surface 432 of the mirror member 430 to the lens 411, an image forming position, at which an image of the end face Wc of the wafer W is formed, can be adjusted onto the imaging device 412, even through there is the optical path difference (see FIG. 15B). Thus, both the images of the peripheral portion Wd of the front surface Wa of the wafer W and the end face Wc of the wafer W, which were imaged by the camera 410, are clear (see FIG. 19C).

As shown in FIGS. 4 to 9 and 20, the back surface imaging subunit 500 includes a camera 510 (imaging means) and an illuminating module 520 (illuminating unit). The camera 510 and the illuminating module 520 constitute a set of imaging modules. The camera 510 includes a lens 511 and one imaging device 512 (e.g., CCD image sensor, CMOS image sensor, etc.). The camera 510 opposes the illuminating module 520 (illuminating unit).

Figure 20:
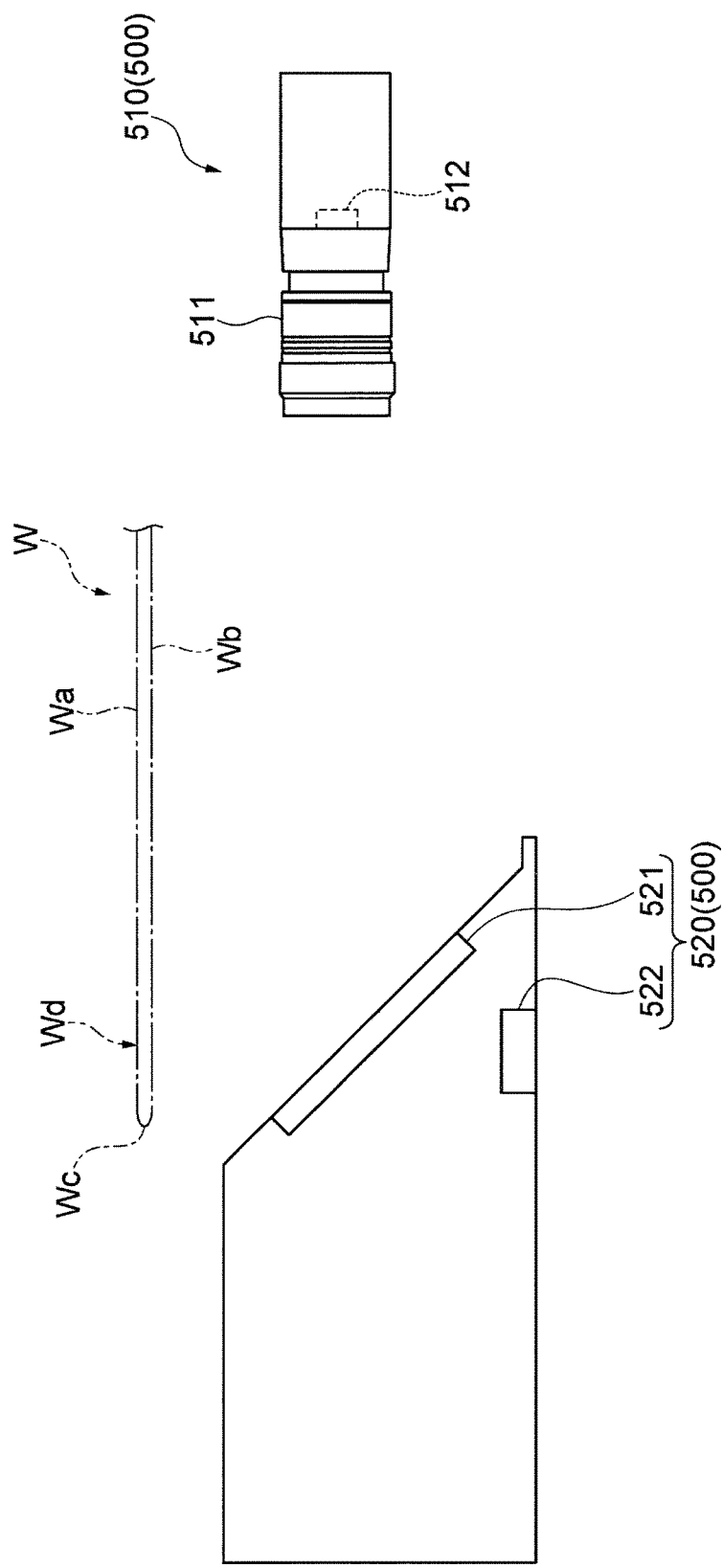
FIG. 20 is a side view of a back surface imaging subunit.

The illuminating module 520 is located below the illuminating module 420, and below the wafer W held by the holding table 201. As shown in FIG. 20, the illuminating module 520 includes a half mirror 521 and a light source 522. The half mirror 521 is inclined at substantially 45° with respect to the horizontal direction. The half mirror 521 has a rectangular shape.

The light source 522 is located below the half mirror 521. The light source 522 is longer than the half mirror 521. Light emitted from the light source 522 passes through the whole half mirror 521 to travel upward. The light having passed through the half mirror 521 is reflected by an object located above the half mirror 521, and is again reflected by the half mirror 521. Then, the light passes through the lens 511 of the camera 510 to enter the imaging device 512 of the camera 510. Namely, the camera 510 can image an object present in an irradiation area of the light source 522 through the half mirror 521. For example, when the wafer W held by the holding table 201 is located at the second position, the camera 510 can image the back surface Wb of the wafer W. Data of the image imaged by the camera 510 are transmitted to the controller 10.

<Structure of Controller>

Figure 21:
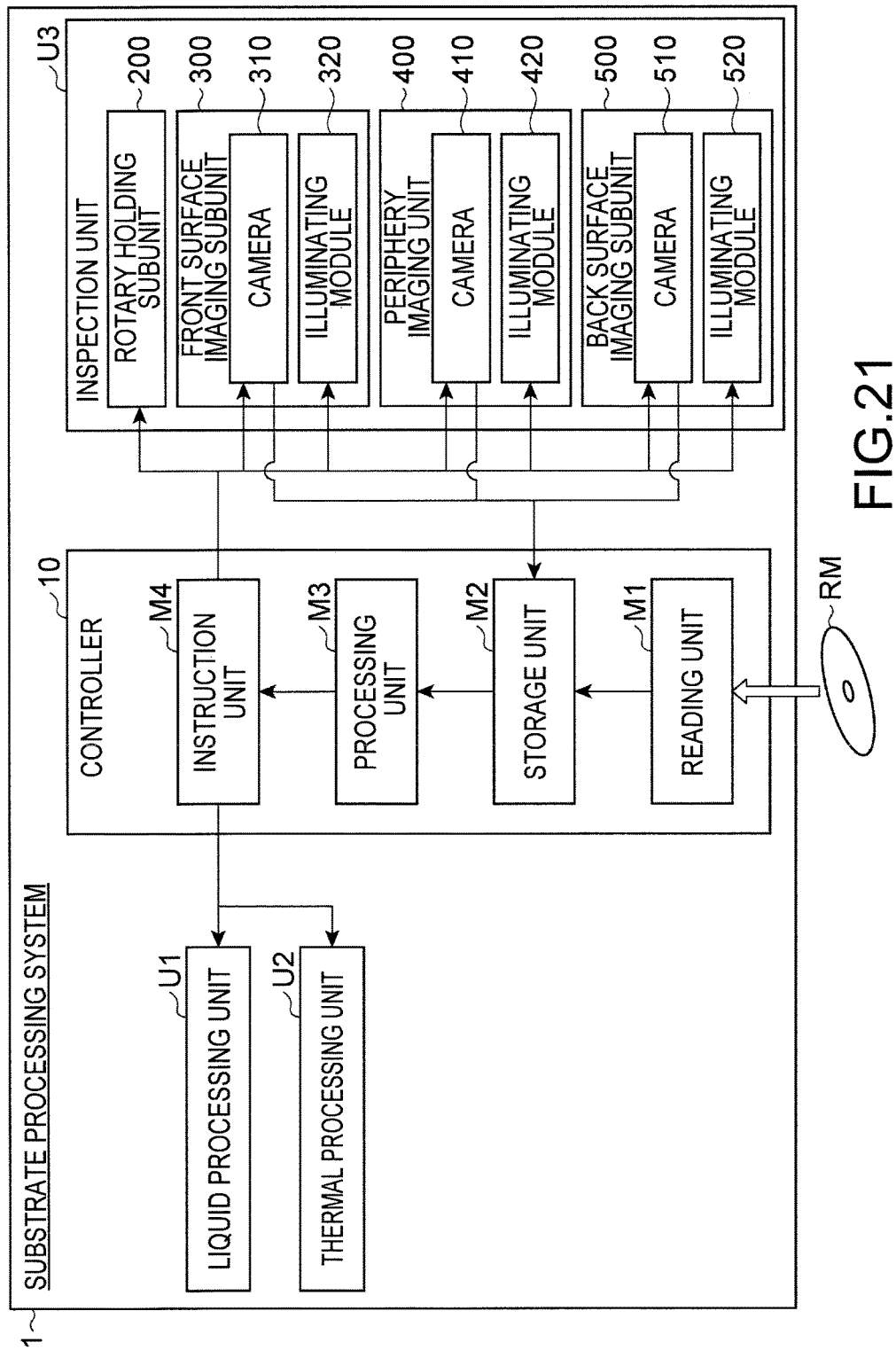
FIG. 21 is a block diagram showing a main part of the substrate processing system.

As shown in FIG. 21, the controller 10 includes, as functional modules, a reading unit M1, a storage unit M2, a processing unit M3 and an instruction unit M4. These functional modules merely correspond to the functions of the controller 10 for the sake of conveniences, and do not necessarily mean that a hardware constituting the controller 10 is divided into these modules. The respective functional modules are not limited to modules whose functions are realized by executing a program, but may be modules whose functions are realized by a dedicated electric circuit (e.g., logic circuit) or an integrated circuit (ASIC: Application Specific Integrated Circuit).

The reading unit M1 reads out a program from a computer-readable recording medium RM. The recording medium RM records a program for operating respective units of the substrate processing system 1. The recording medium RM may be, for example, a semiconductor memory, an optical memory disc, a magnetic memory disc, or a magneto optic memory disc.

The storage unit M2 stores various data. The storage medium M2 stores various data for processing a wafer W (so-called process recipes), set data inputted by an operator through an external input apparatus (not shown) and so on, in addition to a program read out by the reading unit M1 from the recording medium RM and data of images imaged by the cameras 310, 410, 510.

The processing unit M3 processes various data. For example, the processing unit M3 generates, based on various data stored in the storage unit M2, signals for operating the liquid processing unit U1, the thermal processing unit U2 and the inspection unit U3 (for example, the rotary holding subunit 200, cameras 310, 410, 510, illuminating modules 320, 420, 520). In addition, the processing unit M3 processes data of images imaged by the cameras 310, 410, 510, and judges whether a wafer W has a defect or not. If it is judged that the wafer W has a defect, the processing unit M3 generates a signal for stopping the process to the wafer W.

The instruction unit M4 transmits signals generated by the processing unit M3 to the respective apparatuses.

Figure 22:
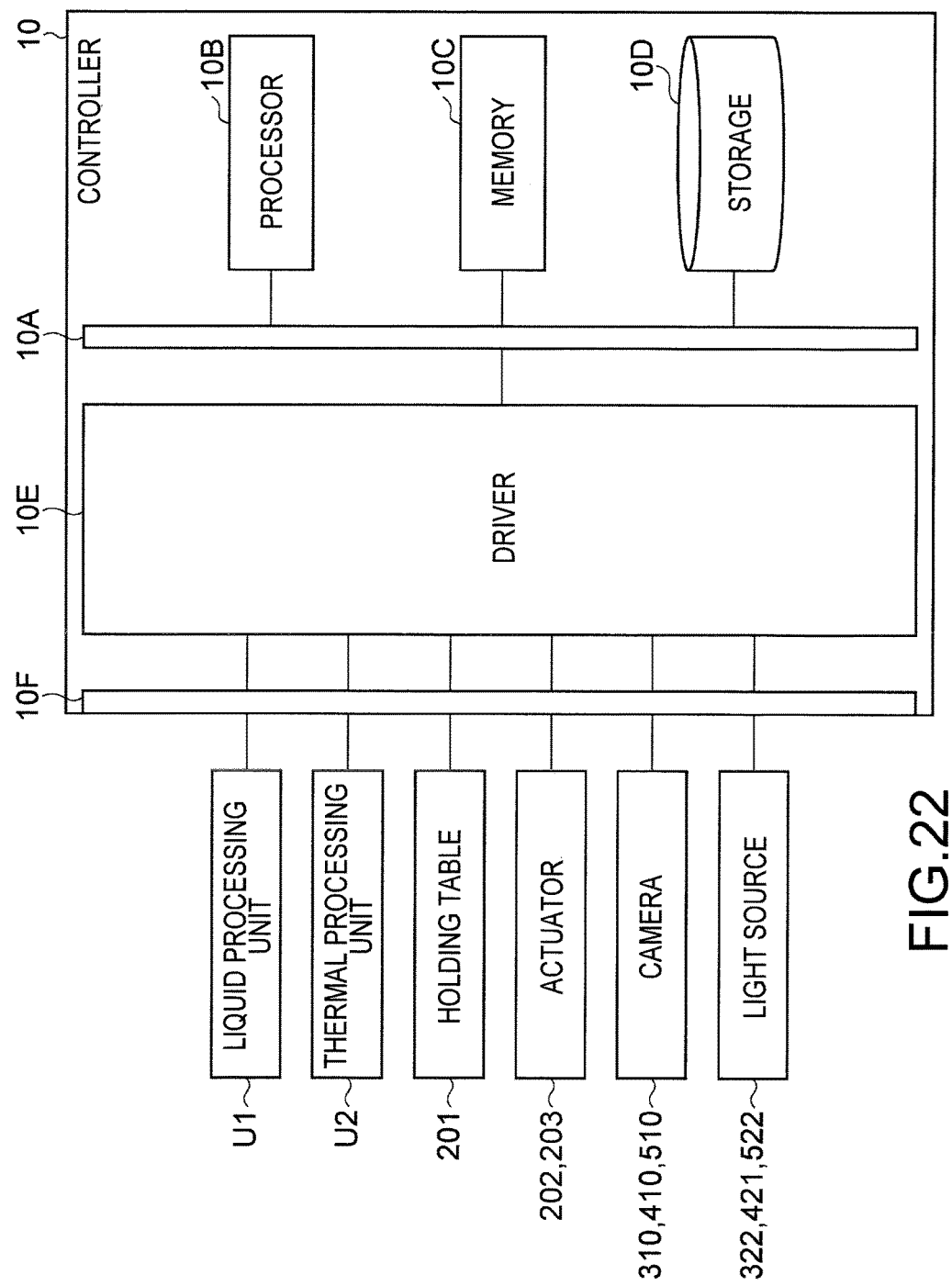
FIG. 22 is a block diagram showing a hardware structure of a controller.

A hardware of the controller 10 is formed of one or more control computer(s), for example. The controller 10 has a circuit 10A as a hardware configuration, which is shown in FIG. 22, for example. The circuit 10A may be formed of an electric circuitry. Specifically, the circuit 10A includes a processor 10B, a memory 10C (storage unit), a storage 10D (storage unit), a driver 10E and an input and output port 10F. The processor 10B cooperates with at least one of the memory 10C and the storage 10D to execute a program, so that a signal is inputted and outputted through the input and output port 10F, whereby the aforementioned respective functional modules are realized. The memory 10C and the storage 10D function as the storage unit M2. The driver 10E is a circuit for driving the respective apparatuses of the substrate processing system 1. Signals are inputted and outputted through the input and output port 10F, between the driver 10E and the various apparatuses of the substrate processing system 1 (for example, rotating unit 21, holding unit 22, pumps 32, 42, valves 33, 42, thermal processing unit U2, holding table 201, actuators 202, 203, cameras 310, 410, 510, light sources 322, 421, 522).

In this embodiment, although the substrate processing system 1 has one controller 10, the substrate processing system 1 may have a group of controllers (control unit) formed of the plurality of controllers 10. When the substrate processing system 1 has a group of controllers, the above-described functional modules may be respectively realized by the one controller 10, or may be realized by a combination of two or more computers 10. When the controller 10 is composed of a plurality of computers (circuits 10A), the above-described functional modules may be realized by one computer (circuit 10A), or may be realized by a combination of two or more computers (circuits 10A). The controller 10 may have the plurality of processors 10B. In this case, the above-described functional modules may be respectively realized by one processor 10B, or may be realized by a combination of two or more processors 10B.

<Operation>

In this embodiment, the mirror member 43 has the reflecting surface 432 that opposes the end face Wc and the peripheral portion Wd of the back surface Wb of the wafer W held by the holding table 201, the reflecting surface 432 being inclined with respect to the rotation axis of the holding table 201. In addition, in this embodiment, the imaging device 412 of the camera 410 receives, through the lens 411, light which comes from the peripheral portion Wd of the front surface Wa of the wafer W held by the holding table 201, and the reflected light which comes from the end face of the wafer W held by the holding table 201 and is reflected by the reflecting surface 432 of the mirror member 430. Thus, both the peripheral portion Wd of the front surface Wa of the wafer W and the end face Wc of the wafer W are simultaneously imaged by the one camera 410. Thus, since plural cameras are no longer necessary, a space for installation of such cameras is unneeded. In addition, since a mechanism for moving the camera 410 is unnecessary, a space for installation of such a mechanism is unneeded. Namely, in this embodiment, the inspection unit U3 can have a significantly simplified structure. As a result, the inspection unit U3 can achieve reduction in size and decrease in cost, while avoiding equipment failure.

In this embodiment, the reflecting surface 432 is a curved surface that is recessed away from the end face Wc of the wafer W held by the holding table 201. Thus, a mirror image of the end face Wc of the wafer W reflected on the reflecting surface 432 is enlarged. For example, if the reflecting surface 432 is not a curved surface, the width of the end face Wc of the wafer W in the image on the imaging device is about 20 pixels. On the other hand, if the reflecting surface 432 is a curved surface as described above, the width of the end face Wc of the wafer W in the image on the imaging device is enlarged about 1.5 times in the thickness direction. Thus, a more detailed image of the end face Wc of the wafer W can be obtained. As a result, by processing the detailed image, the end face Wc of the wafer W can be more precisely inspected.

The optical path length of light, which comes from the end face Wc of the wafer W and is reflected by the reflecting surface 432 of the mirror member 430 to reach the lens 411, is longer than the optical path length of light, which comes from the peripheral portion Wd of the front surface Wa of the wafer W to reach the lens 411, because of the reflection by the mirror member 430. However, in this embodiment, the focus adjusting lens 427 is disposed in the optical path of the light extending from the reflecting surface 432 of the mirror member 430 to the lens 411. The focus adjusting lens 427 is configured to adjust an image forming position, at which the image of the end face Wc of the wafer W is formed, onto the imaging device 412. Thus, owing to the focus adjusting lens 427, the image forming position of the end face Wc of the wafer W can be adjusted onto the imaging device 412, whereby both the images of the peripheral portion Wd of the front surface Wa of the wafer W and the end face Wc of the wafer W are clear. As a result, by processing the clear image, the end face Wc of the wafer W can be more precisely inspected.

In this embodiment, the illuminating module 420 irradiates the reflecting surface 432 of the mirror member 430 with diffused light in order to allow the diffused light from the illuminating module 420 which is reflected by the reflecting surface 432 of the mirror member 430, to fall on the end face Wc of the wafer W held by the holding table 201. Thus, the diffused light enters the end face Wc of the wafer W from various directions. Thus, the entire end face Wc of the wafer W can be uniformly illuminated. As a result, the end face Wc of the wafer W can be imaged more clearly.

In this embodiment, light emitted from the light source 421 is scattered by the light scattering member 422, enlarged by the cylindrical lens 425 and further diffused by the light diffusing member 426. Thus, the diffused light enters the end face Wc of the wafer W from various directions. Thus, the entire end face Wc of the wafer W can be uniformly illuminated. As a result, the end face Wc of the wafer W can be imaged more clearly.

OTHER EMBODIMENTS

The embodiment according to the disclosure has been described in detail, but the above embodiment can be variously modified within the scope of the present invention. For example, as long as the reflecting surface 432 is inclined with respect to the rotation axis of the holding table 201 and opposes the end surface Wc and the back surface Wb of the wafer W held by the holding table 201, the reflecting surface 432 has another shape (e.g., flat shape) other than a curved face.

It is not necessary for the periphery imaging subunit 400 to include the focus adjusting lens 427.

It is not necessary for the periphery imaging subunit 400 to include any of the light scattering member 422, the cylindrical lens 425 and the light diffusing member 426.

The inspection unit U3 may be disposed in the shelf units U10, U11. For example, the inspection unit U3 may be provided in the cells of the shelf units U10, U11, which are located correspondingly to the unit processing units 14 to 17. In this case, a wafer W is directly delivered to the inspection unit U3 by the arms A1 to A8 that transport the wafer W.

What is claimed is:

1. A substrate imaging apparatus comprising:
   a rotary holding unit that holds and rotates a substrate about a rotation axis;
   a mirror member having a reflecting surface that opposes an apex of the substrate and a peripheral portion of a back surface of the substrate held by the rotary holding unit, the reflecting surface being inclined with respect to a rotation axis of the rotary holding unit; and
   a camera having an imaging device that receives both first light and second light through a lens,
   wherein the mirror member and the camera are configured and disposed such that:
   the first light having been reflected by an inner peripheral portion of a front surface of the substrate held by the rotary holding unit comes into the camera without being reflected by the mirror member, the inner peripheral portion extending in a plane perpendicular to the rotation axis of the substrate;

the second light having been reflected by an outer peripheral portion of the substrate held by the rotary holding unit is reflected by the mirror member and then comes into the camera, with the outer peripheral portion extending radially outside the inner peripheral portion so as to be inclined with respect to the inner peripheral portion and containing the apex; and the first light and the second light come into the same imaging device of the same camera.

2. The substrate imaging apparatus according to claim 1, wherein the reflecting surface is a curved surface that is recessed away from the apex of the substrate held by the rotary holding unit.

3. The substrate imaging apparatus according to claim 2, further comprising a focus adjusting lens disposed in an optical path of the second light extending from the reflecting surface to the lens in order to adjust an image forming position, at which an image of the apex of the substrate is formed, onto the imaging device.

4. The substrate imaging apparatus according to claim 3, further comprising an illuminating unit including a light source and a light diffusing member that diffuses light from the light source toward a first direction perpendicular to an optical axis of the light from the light source in order to generate diffused light, wherein the illuminating unit irradiates the inner peripheral portion of the front surface of the substrate held by the rotary holding unit with the diffused light, and irradiates the reflecting surface of the mirror member with the diffused light in order to allow the diffused light reflected by the mirror member to fall on the apex of the substrate held by the rotary holding unit.

5. The substrate imaging apparatus according to claim 4, wherein the illuminating unit further includes:

a light scattering member that scatters the light from the light source to generate scattered light; and a cylindrical lens that allows the scattered light from the light scattering member to pass through the light diffusing member, the cylindrical lens being convex toward the light diffusing member, wherein the cylindrical lens diffuses light coming into the cylindrical lens toward a second direction perpendicular to an optical axis of the light emitted from the light source and perpendicular to the first direction.

6. The substrate imaging apparatus according to claim 2, further comprising an illuminating unit including a light source and a light diffusing member that diffuses light from the light source toward a first direction perpendicular to an optical axis of the light from the light source in order to generate diffused light, wherein the illuminating unit irradiates the inner peripheral portion of the front surface of the substrate held by the rotary holding unit with the diffused light, and irradiates the reflecting surface of the mirror member with the diffused light in order to allow the diffused light reflected by the mirror member to fall on the apex of the substrate held by the rotary holding unit.

7. The substrate imaging apparatus according to claim 6, wherein the illuminating unit further includes:

a light scattering member that scatters the light from the light source to generate scattered light; and a cylindrical lens that allows the scattered light from the light scattering member to pass through the light diffusing member, the cylindrical lens being convex toward the light diffusing member, wherein the cylindrical lens diffuses light coming into the cylindrical lens toward a second direction perpendicular to an optical axis of the light emitted from the light source and perpendicular to the first direction.

8. The substrate imaging apparatus according to claim 1, further comprising a focus adjusting lens disposed in an optical path of the second light extending from the reflecting surface to the lens in order to adjust an image forming position, at which an image of the apex of the substrate is formed, onto the imaging device.

9. The substrate imaging apparatus according to claim 8, further comprising an illuminating unit including a light source and a light diffusing member that diffuses light from the light source toward a first direction perpendicular to an optical axis of the light from the light source in order to generate diffused light, wherein the illuminating unit irradiates the inner peripheral portion of the front surface of the substrate held by the rotary holding unit with the diffused light, and irradiates the reflecting surface of the mirror member with the diffused light in order to allow the diffused light reflected by the mirror member to fall on the apex of the substrate held by the rotary holding unit.

10. The substrate imaging apparatus according to claim 9, wherein the illuminating unit further includes:

a light scattering member that scatters the light from the light source to generate scattered light; and a cylindrical lens that allows the scattered light from the light scattering member to pass through the light diffusing member, the cylindrical lens being convex toward the light diffusing member, wherein the cylindrical lens diffuses light coming into the cylindrical lens toward a second direction perpendicular to an optical axis of the light emitted from the light source and perpendicular to the first direction.

11. The substrate imaging apparatus according to claim 1, further comprising an illuminating unit including a light source and a light diffusing member that diffuses light from the light source toward a first direction perpendicular to an optical axis of the light from the light source in order to generate diffused light, wherein the illuminating unit irradiates the inner peripheral portion of the front surface of the substrate held by the rotary holding unit with the diffused light, and irradiates the reflecting surface of the mirror member with the diffused light in order to allow the diffused light reflected by the mirror member to fall on the apex of the substrate held by the rotary holding unit.

12. The substrate imaging apparatus according to claim 11, wherein the illuminating unit further includes:

a light scattering member that scatters the light from the light source to generate scattered light; and a cylindrical lens that allows the scattered light from the light scattering member to pass through the light diffusing member, the cylindrical lens being convex toward the light diffusing member, wherein the cylindrical lens diffuses light coming into the cylindrical lens toward a second direction perpendicular to an optical axis of the light emitted from the light source and perpendicular to the first direction.

* * * * *